US012776038B2

(12) United States Patent
Zhukauskas et al.

(10) Patent No.: US 12,776,038 B2
(45) Date of Patent: Oct. 27, 2026

(54) METHODS FOR ANALYZING A PROCESSED NERVE GRAFT

(71) Applicant: Axogen Corporation, Alachua, FL (US)

(72) Inventors: Rasa Zhukauskas, Gainesville, FL (US); Xavier E. Cortez, High Springs, FL (US); Jonathan D. Gatson, Gainesville, FL (US)

(73) Assignee: Axogen Corporation, Alachua, FL (US)

( * ) Notice: Subject to any disclaimer, the term of this patent is extended or adjusted under 35 U.S.C. 154(b) by 176 days.

(21) Appl. No.: 18/917,091

(22) Filed: Oct. 16, 2024

(65) Prior Publication Data

US 2025/0124576 A1 Apr. 17, 2025

Related U.S. Application Data

(60) Provisional application No. 63/544,548, filed on Oct. 17, 2023.

(51) Int. Cl.
*G06T 7/00* (2017.01)
*A61B 17/11* (2006.01)

(52) U.S. Cl.
CPC ........ *G06T 7/0014* (2013.01); *A61B 17/1128* (2013.01)

(58) Field of Classification Search
None
See application file for complete search history.

(56) References Cited

U.S. PATENT DOCUMENTS

| | | | | |
|---|---|---|---|---|
| 2010/0268336 | A1 | 10/2010 | English et al. | |
| 2014/0248325 | A1 | 9/2014 | Schmidt et al. | |
| 2016/0339148 | A1* | 11/2016 | Muir | A61K 38/51 |
| 2016/0350918 | A1* | 12/2016 | Deister | G06T 7/62 |
| 2018/0353653 | A1* | 12/2018 | Reid | A61L 27/20 |
| 2021/0205460 | A1* | 7/2021 | Lang | A61K 47/42 |
| 2024/0412324 | A1* | 12/2024 | Wong | G06T 3/4046 |
| 2025/0124576 | A1* | 4/2025 | Zhukauskas | G06T 7/0012 |

FOREIGN PATENT DOCUMENTS

| | | | | | |
|---|---|---|---|---|---|
| CA | 2447139 | C | * | 11/2013 | A61K 39/39541 |
| CA | 3040518 | A1 | * | 4/2018 | G06T 7/187 |
| WO | WO-2022272014 | A1 | * | 12/2022 | G06T 7/62 |
| WO | WO-2024228936 | A1 | * | 11/2024 | A61K 51/088 |

OTHER PUBLICATIONS

International Search report and Written Opinion issued in International Application No. PCT/US2024/051511, date of mailing: Dec. 6, 2024, 8 pages.

* cited by examiner

*Primary Examiner* — Ricky Chin
(74) *Attorney, Agent, or Firm* — Bookoff McAndrews, PLLC

(57) ABSTRACT

The invention provides automated methods for analyzing and quantifying the clearance of chondroitin sulfate proteoglycans (CSPGs) from a processed nerve graft tissue sample.

23 Claims, 18 Drawing Sheets

RGB Image Conversion Algorithm Workflow

| | A | B | C | D | E | F | G | H |
|---|---|---|---|---|---|---|---|---|
| 1 | | Image ID | Image Compression | Image Resolution (um/pixel) | Image Pixel Count | Pixels Analyzed | Positive DAB Staining (%) | Negative DAB Staining (%) |
| 2 | 1 | 179389_A_RGB.tif | Uncompressed | 0.5039 | 107956449 | 26429077 | 35.25783 | 64.74217 |
| 3 | 2 | 179389_B_RGB.tif | Uncompressed | 0.5039 | 100542024 | 18419380 | 12.42127 | 87.57873 |
| 4 | 3 | 179389_C_RGB.tif | Uncompressed | 0.5039 | 99397155 | 20285652 | 26.32679 | 73.67321 |
| 5 | 4 | 179389_D_RGB.tif | Uncompressed | 0.5039 | 29671428 | 2972233 | 11.08237 | 88.91763 |
| 6 | 5 | 179389_E_RGB.tif | Uncompressed | 0.5039 | 37480770 | 2702012 | 17.40995 | 82.59005 |
| 7 | 6 | 179389_F_RGB.tif | Uncompressed | 0.5039 | 41564365 | 4830680 | 24.09549 | 75.90451 |
| 8 | 7 | 179389_PC_RGB.tif | Uncompressed | 0.5039 | 147776440 | 62882947 | 72.0913 | 27.9087 |

FIG. 9B

*IHC Profiler* staining vectors:

Vectors determined from single-stained Avance Nerve Graft images:

METHODS FOR ANALYZING A PROCESSED NERVE GRAFT

CROSS-REFERENCE TO RELATED APPLICATIONS

This application claims priority to, and the benefit of, U.S. Provisional Application No. 63/544,548, filed Oct. 17, 2023, the content of which is incorporated by reference herein in its entirety.

FIELD OF THE INVENTION

The invention generally relates to automated methods for assessing the quality of a processed nerve graft, and, in particular, quantifying chondroitin sulfate proteoglycan (CSPG) clearance from a processed nerve graft tissue sample.

BACKGROUND

Nerves can be subject to damage, for example crushing or severing, through accident, injury, and during surgery, among other things. Techniques for the surgical repair of damaged nerves include, when needing to connect severed nerve ends, direct nerve repair for small gaps, and the use of nerve grafts for larger gaps in a nerve.

Progress has been made in understanding the post-injury tissue response, especially the identification and characterization of molecules at the lesion site that inhibit axonal regeneration. The post-injury environment is inhibitory to the process of nerve regeneration due in part to axonal and myelin debris and the increased presence of, e.g., chondroitin sulfate proteoglycans that have growth-inhibitory effects. While the axonal segment proximal to the site of the injury can regenerate new axonal sprouts, certain elements have been found to inhibit axonal regeneration and/or remyelination, including, but not limited to, chondroitin sulfate proteoglycans (CSPGs). Substantial evidence indicates that the clearance of such elements improves axonal growth in the distal nerve segment.

Thus, the enhancement of nerve regeneration through, e.g., nerve grafts, may be improved by removing to some extent in part or in full, i.e., effectively clearing the nerve graft of, CSPGs before surgically implanting the graft into the repair site. There exists a need for quantitatively evaluating such clearance, and the extent of such clearance, in assessing the quality of a nerve graft.

SUMMARY

The present invention provides automated methods for analyzing and quantifying the maintenance and/or clearance of certain stainable-components of tissue in the tissue, after the tissue is subjected to one or more processing steps. In one such embodiment, the present invention provides automated methods of analyzing and quantifying the clearance of chondroitin sulfate proteoglycans (CSPGs) from a processed nerve graft tissue sample. The present invention addresses the challenges associated with analysis of processed nerve graft tissue by providing methods that are automated, quantitative, highly accurate, and eliminate the human bias/error of the technician.

A processed nerve graft supports and directs the growing axon segments with supporting structures, while providing a pathway clear of axonal and myelin debris. Processed nerve grafts, having a structure and composition similar to a nerve fascicle, such as with the Avance® nerve graft, assist in axonal regeneration by providing a scaffold through which new axon segments can grow. The enhanced removal of components, such as CSPGs from the graft, further enhances the efficacy of the graft and provides an environment more conducive to enhanced axonal regeneration after implantation.

Methods of the invention provide for automated, quantitative analysis of the quality of a processed nerve graft. In particular, the methods of the invention provide automated methods for histology image analysis for determining the clearance of CSPGs from the processed nerve graft. Additionally, the methods of the invention provide for performing a quality control evaluation of nerve tissue that has been chemically or otherwise processed to determine the level and sufficiency of the processing of the tissue and the quantitative assessment of the presence of certain tissue components, and/or the extent of removal of components that are inhibitory to regeneration. Evaluation using the histology-based image analysis methods may be used to assess the preservation of endoneurial tube structure, clearance of cells and cellular debris, and clearance of CSPG, including to ensure the manufacturing process of nerve grafts consistently produces a product that meets stringent quality specifications.

In particular embodiments, the methods of the invention provide for determining CSPG clearance from a processed nerve graft tissue sample. CSPGs are a proteoglycan consisting of a protein core and chondroitin sulfate side chain. CSPGs are structural components of many human and animal tissues, including nerve tissue. CSPGs are widely expressed in a normal nervous system, serving as guidance cues during development and modulating synaptic connections in an adult. With injury or disease, an increase in CSPG expression is commonly observed close to lesioned areas. However, such CSPG deposits form a substantial barrier to regeneration and are largely responsible for the inability to repair damage. Accordingly, CSPGs play a significant role in limiting the reparative response. In particular, CSPGs are known to inhibit axon regeneration after, e.g., spinal cord injury and to contribute to glial scar formation post injury by acting as a barrier against new axons growing into the injury site. In peripheral nerve tissue, CSPGs may generally be localized to the extracellular matrix, especially the endoneurial tubes.

Thus, the efficacy of the process that cleaves CSPG sugar side chains may be evaluated using the automated image analysis of histological immunochemistry (IHC) samples provided by methods of the invention. The CSPG image analysis method is a quantitative method for determining the level of CSPG clearance from a processed nerve graft by performing image analysis on digital images of CSPG-stained slides. CSPG IHC staining is used to stain native CSPGs using antigen specific primary antibody and appropriate secondary antibody which reacts with the primary antibody at the location of the CSPG antigens in the tissue. This reaction is then identified with a brown color through DAB immunoperoxidase reaction. An image analysis algorithm is used to quantify the proportions of the sample that are positively or negatively stained for DAB. In some embodiments, only specific CSPG side chains that inhibit axonal growth are stained.

For example, in some embodiments, the automated image analysis of methods of the invention provide a direct measure of DAB staining in processed nerve graft histological samples, which directly correlates to the level of presence of CSPG in the sample. Thus, the present invention addresses the challenges of manufacturing a product that consistently meets specifications and provides quantitative methods for evaluating residual CSPG that allows for a more accurate and efficient manufacturing process.

In one aspect, the invention provides an automated method for assessing CSPG clearance from a processed nerve graft tissue sample. The method includes receiving a digital immunohistochemistry (IHC)-stained image of a nerve graft tissue, wherein, the IHC-stained image comprising at least hematoxylin staining and 3,3'-Diaminobenzidine (DAB) staining, and generating a digital RGB color image of one or more selected regions of the stained image using an image conversion algorithm. Further, the method includes performing, using an image analysis algorithm, image processing techniques such as color deconvolution, to digitally separate stains such as hematoxylin and DAB from a color image. In some embodiments, the method includes performing, using an image analysis algorithm, a color deconvolution on the one or more selected regions to thereby separate image colors into a hematoxylin image channel, a DAB image channel, and a residual image channel; analyzing pixel intensity values of the image colors of one or more of the image channels based, at least in part, on image processing parameters to determine a number of pixels in one or more of a positive staining region, a negative staining region, and an unstained region in each image channel; and quantifying at least a proportion of the number of pixels analyzed as DAB positive-stained pixels in the positive staining region and DAB negative-stained pixels in the negative stained region in relation to a total number of pixels analyzed to thereby determine CSPG clearance in the processed nerve graft tissue sample.

In some embodiments, a calculated percent of DAB negative-stained pixels correlates to removal of CSPG in the processed nerve graft tissue sample. In some embodiments, a calculated percent of DAB positive-stained pixels correlates to the presence of CSPG in the processed nerve graft tissue sample.

In some embodiments, for the hematoxylin image channel, the image produced represents the hematoxylin staining in the IHC-stained image, and wherein the image processing step subtracts the DAB staining from the IHC-stained image.

In some embodiments, for the DAB image channel, the image produced after the image processing step represents the DAB staining in the IHC-stained image, and wherein the image processing step separates the hematoxylin staining from the IHC-stained image.

In some embodiments, for the residual image channel, the image produced after the color deconvolution step represents the residual of the color deconvolution process.

In some embodiments, the analyzing step comprises analyzing the pixel intensity values in the image channel for any color in the range from 0 to 255 inclusive, wherein a pixel intensity value of 0 represents a darkest shade of color and a pixel intensity value of 255 represents a lightest shade of color. The total pixels analyzed comprises the number of pixel intensity values between 0 and 235 inclusive analyzed, in some embodiments. The positive staining regions comprise pixel intensity values between 0 and 180 inclusive, in some embodiments. In particular embodiments, the percent DAB positive-stained pixels is the proportion of pixels in the DAB image channel having an intensity value between 0 and 180 inclusive that represent positive DAB staining as compared to the total pixels analyzed.

Further, in some embodiments, the negative staining regions comprise pixel intensity values between 181 and 235 inclusive. Further, the percent negative DAB staining is the proportion of pixel intensity values in the DAB image channel with intensity value between 181 and 235 inclusive that represent negative DAB staining as compared to the total pixels analyzed, in some embodiments. In some embodiments, the unstained regions comprise pixels between 236 and 255 inclusive intensity values, wherein the pixels represent absence of extracellular matrix (ECM) tissue and are excluded from the analysis.

In some embodiments, the image processing parameters are determined via analysis of a library of images comprising single CSPG-stained sections of peripheral nerve graft tissue samples, wherein analysis of the library of single CSPG-stained sections of peripheral nerve graft tissue samples determines an optimal separation of image colors and a range of pixel intensity values. For example, in some embodiments, the image processing parameters comprise optimized staining vectors comprising a three-color vector matrix representing red, green, and blue absorbances in a saturated region of each individual image channel, wherein the optimized staining vectors optimize the method for application to processed nerve graft tissue.

In particular embodiments, the processed nerve graft tissue comprises decellularized and sterile ECM processed from human peripheral nerve tissue having undergone a proprietary processing step which cleaves sulfated sugar side chains from a CSPG protein, wherein the immunohistochemistry staining is used to stain remaining chondroitin sulfate side chains a brown color through a DAB immunoperoxidase reaction, and wherein evaluation of CSPG clearance is used for quality control testing for a processed nerve graft tissue production lot. Further, in some embodiments, the sulfated sugar side chains comprise one or more of chondroitin 4-sulfate, chondroitin 6-sulfate, and dermatan sulfate. In particular embodiments, a lot average percent negative DAB staining establishes an acceptance criteria for the production lot of processed nerve graft tissue.

In some embodiments, the method further comprises batch processing of a plurality of digital IHC-stained images, wherein a batch of images are analyzed at once.

In some embodiments, the digital IHC-stained image is an extracted image in an uncompressed TIF file type of each individual sample extracted from a whole slide scan.

BRIEF DESCRIPTION OF THE DRAWINGS

FIG. 9B shows an output format of the calculated image information.

DETAILED DESCRIPTION

Figure 1:
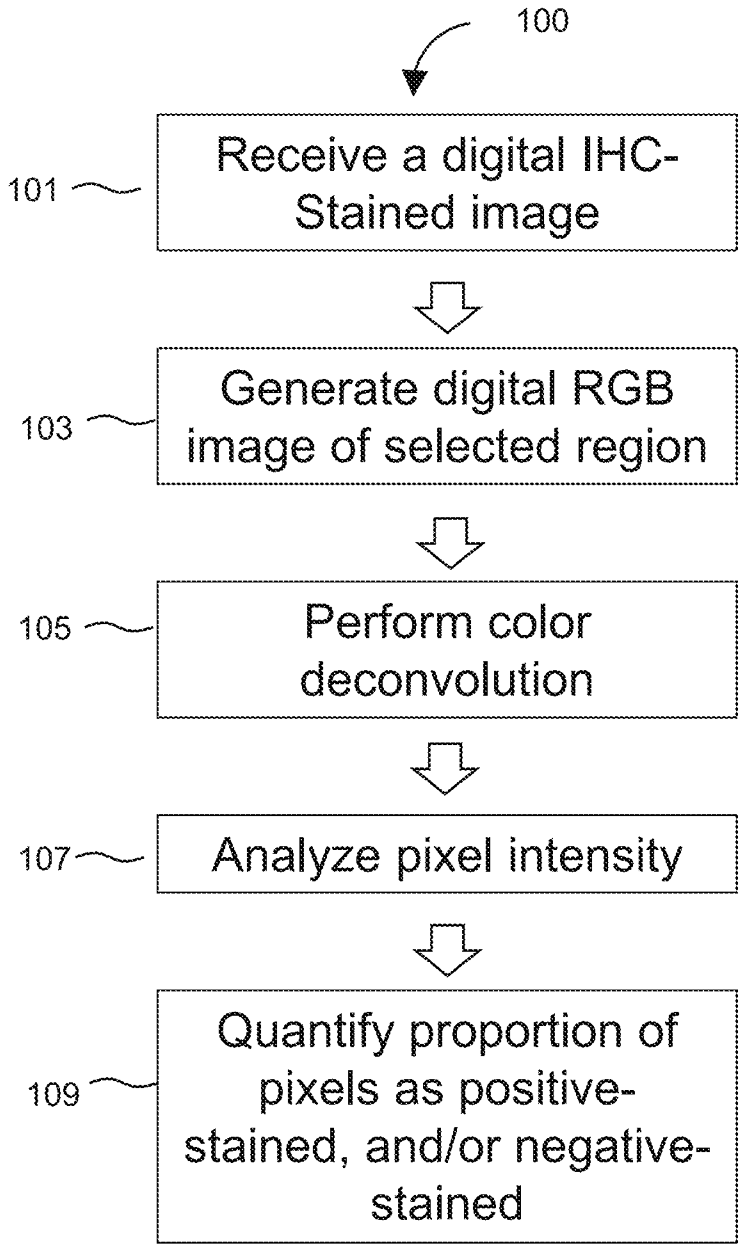
FIG. 1 illustrates a method according to one embodiment of the invention.

There is a critical need for quantifying nerve graft quality. Human nerve tissue used, for example, as an implant like Avance®, is processed in a manner that preserves the essential structure of the extracellular matrix (ECM) while cleansing away cells and cellular debris and other components that may produce an immune response or otherwise be detrimental to axonal extension and nerve regeneration. Histology-based analytical methods may be used to assess the efficacy of manufacture of nerve graft lots for preservation of endoneurial tube structure, clearance of cells and cellular debris, and clearance of chondroitin sulfate proteoglycan. Thus, methods of the invention may be used in conjunction with a histology monitoring program to assess that the manufacturing process of a tissue implant consistently produces a product that meets specifications.

In particular, the invention provides automated methods for quantitative image analysis, based on algorithmic determination of image processing parameters, that separates histological staining in a color deconvolution process. As is described in detail herein, the methods of the invention provide for optimization of histogram profiling to determine the proportion of pixels that are positively and negatively stained with a chromogen, for example 3,3'-Diaminobenzidine (DAB). The methods provide for an automated and optimized histological image analysis intended to quantify the presence of particular staining in a slide image.

The methods may be applied to any immunostaining method where, for example, DAB is used as a chromogen to identify antigen-antibody reaction and hematoxylin is used as a counterstain. In the case of nerves, the methods of the present invention to quantify the maintenance of and/or level of clearance of one or more tissue components may be applied to proteins, including, but not limited to, Neurofilament, alpha- and beta-Tubulins, Actins (F-Actin), GAP-43, Collagen types I, III, IV, V, Fibronectin, Elastin, and myelin related components such as Myelin basic protein, myelin associated glycolipids and proteolipids, sugar side chains, and any other nerve structural protein or other type of component of interest (proteoglycans, growth factors, etc.).

In some embodiments, the methods of the present invention may be applied to proteins associated with the basement membrane of nerve tissue, including, but not limited to, laminin (e.g., laminin alpha-1, laminin alpha-2, laminin alpha-4, laminin alpha-5, laminin beta-1, laminin beta-2, laminin gamma-1), collagen (e.g., collagen IV alpha-1 (IV) chain, collagen IV alpha-1/5 (IV) chain, collagen alpha IV-2 chain, collagen alpha IV-3 chain), fibronectin (e.g., fibronectin 1 (type-III 4,7 domain)), perlecan, and nidogen (e.g., nidogen-1, nidogen-2).

In some embodiments, the methods of the present invention may be applied to other nerve-related proteins, including, but not limited to: collagen I alpha-1 chain; collagen alpha-2 (I) chain; collagen alpha-3 (VI) chain; lumican; collagen alpha-1 (VI) chain; collagen alpha-1 (XXVIII) chain; dermatopontin; collagen alpha-1 (III) chain; collagen alpha-3 (V) chain; keratin; type-II cytoskeletal 1; fibrillin-1; decorin; collagen alpha-1 (XVI) chain; vitronectin; collagen alpha-1 (XXXI) chain; myelin proteins P0; collagen alpha-2 (VI) chain; collagen alpha-1 (VIII) chain; asporin; collagen alpha-1 (V) chain; prolargin; biglycan; collagen alpha-1 (II) chain; myelin P2 protein; periostin; collagen alpha-1 (XIV) chain; alpha-crystallin B chain; and/or collagen alpha-1 (XII) chain.

Immunohistochemistry (IHC)-Stained Sample Images

Methods of the invention may be used for digital IHC-stained images of different tissues of different origin. IHC staining is a method for detecting antigens or haptens in histological tissue sections by exploiting the principle of antibodies binding specifically to antigens in biological tissues. The antibody-antigen binding may be visualized in different manners (e.g., fluorescent detection or chromogenic detection). The basic underlying principle of these techniques is the staining of tissue samples with antibodies specific to the molecular marker of interest. In an IHC method, visualization of the antibody-antigen reaction is accomplished by the use of a secondary antibody conjugated to an enzyme, such as a peroxidase, for example, horseradish peroxidase (HRP), which catalyzes a brown color-producing reaction. In IHC, HRP is conjugated to either a primary or secondary antibody targeting and reacted with its substrate with the intention of using the colored precipitate to inform the analysis of the location and quantity of a target antigen in a tissue section.

A chromogen, such as 3,3'-Diaminobenzidine (DAB) may be used in the IHC staining. DAB reacts with, for example, HRP in the presence of peroxide to yield an insoluble, brown-colored product at locations where peroxidase-conjugated antibodies are bound to samples. The brown precipitate is insoluble in alcohol and other organic solvents, making it an excellent substrate for immunohistochemical staining.

Further, a nuclear stain formulation of hematoxylin and eosin may be used as part of the IHC-staining process as a counterstain. Hematoxylin has a deep blue-purple color and stains nucleic acids and chromatin (cell nuclei). Eosin is a pink counterstain that stains cytoplasm. For example, in a typical tissue sample, cell nuclei are stained blue and the cytoplasm and extracellular matrix have varying degrees of pink staining.

Methods for Assessing CSPG Clearance

FIG. 1 illustrates a method according to one embodiment of the invention. In some aspects, methods of the invention may be used for assessing chondroitin sulfate proteoglycan (CSPG) clearance from a processed nerve graft tissue sample. In a nonlimiting example, the methods of the invention may be used to perform a quality control evaluation of nerve tissue that has been processed by a chemical or other method to evaluate whether the processing procedure was effective and meets quality control specifications. The methods may also be used to quantify the extent of removal of CSPGs from the sample. The automated image analysis method is unique in that it may be applied to digital images of anti-CSPG IHC stained histology sections of processed nerve graft tissue and is optimized for unique images produced in relation to the IHC-staining protocols used for evaluation of processed nerve grafts during manufacture of a biologic implant. As noted, the applicability of methods of the invention may be applied to the assessment of the level of clearance of other components of tissue, for example, the presence of certain tissue components, and/or the removal of components that are inhibitory to regeneration. Methods of the invention may also be applied to the assessment of the level of maintenance of other components of the tissue after processing, for example preservation of endoneurial tube structure, preservation of structural proteins and proteoglycans. Thus, methods of the invention may be applied to quantifying the maintenance and/or clearance of certain stainable-components of tissue in the tissue, after the tissue is subjected to one or more processing steps.

Tissue may be harvested from a human, or from another source such as, but not limited to, e.g., an animal or reptile, and may be from a donor, including from a cadaver, and may be cleaned and processed, for example to remove fat and/or other extraneous, non-nerve tissue and components, including antigens, to isolate the desired tissue. The harvested nerve tissue may be subjected to various chemical and enzymatic processes to decellularize the tissue. As noted, one particularly challenging aspect of tissue engineering is the production of nerve grafts that can be used to help regeneration of severed nerves. Removal of residual cellular material minimizes pathogens in the tissue and eliminates immunogenic material that might lead to graft immunorejection. Consequently, processing methods used for nerve grafts involve decellularization techniques. Processing methods may also encompass steps for removal of other graft components which might otherwise negatively impact nerve regeneration, for example, the removal of CSPGs.

CSPG is a proteoglycan consisting of a protein core and chondroitin sulfate side chain. CSPGs are known to be structural components of many human and animal tissues, including nerve tissue. In peripheral nerve tissue, for example, CSPGs are localized in the extracellular matrix, especially the endoneurial tubes. The endoneurial tube is a thin layer of extracellular matrix covering the Schwan cell/axon complex. It is a continuous cylinder through which regenerating axons grow through. Also known as basal lamina tubes or Schwann cell basal lamina. The extracellular matrix is a three-dimensional network of extracellular macromolecules, such as collagen, enzymes, and glycoproteins, that provide structural and biochemical support to surrounding cells. In the context of processed nerve grafts, ECM refers to the three-dimensional architecture inherent to human peripheral nerve tissue (epineurium, fascicles, perineurium, and endoneurial tubes). Laminins are large cruciform glycoproteins that are composed of one alpha, one beta, and one gamma chain. Laminin is a major component of the endoneurial tubes of the nerve tissue, which is the structure processed nerve graft is intended to preserve. Laminin is found on the inner, abaxonal surface of the endoneurial tubes. Laminin has been shown to play a critical role in the promotion and guidance of axonal regeneration in peripheral nerve tissue.

The majority of CSPGs can interact with growth factors, cell adhesion molecules, and other ECM molecules in the local environment and may regulate their biological activity. Some CSPGs have inhibitory effects on axonal regeneration, with the inhibitory nature of individual CSPG molecules varying among the proteoglycans. CSPGs are shown to inhibit axon regeneration after spinal cord injury and to contribute to glial scar formation post injury by acting as a barrier against new axons growing into the injury site. Thus, the manufacture of a processed nerve graft may include an enzyme treatment step which cleaves the sulfated sugar side chains from the chondroitin sulfate proteoglycan core protein in the peripheral nerve tissue. The enzyme treatment may cleave chondroitin 4-sulfate, chondroitin 6-sulfate and dermatan sulfate) from the chondroitin sulfate proteoglycan core protein in peripheral nerve tissue.

Anti-CSPG immunohistochemistry staining may then be used to monitor the removal of CSPG in an individual sample and/or a nerve graft production lot. The IHC staining protocol may use, for example, a monoclonal anti-chondroitin sulfate antibody. The anti-chondroitin sulfate antibody may recognize chondroitin sulfate type A (chondroitin-4-sulfate) and type C (chondroitin-6-sulfate). The IHC staining protocol may use DAB as a chromogen to stain areas abundant in chondroitin sulfate side chains a brown color. In some embodiments, only specific CSPG side chains that inhibit axonal growth are stained.

In one aspect, the invention provides an automated method for assessing chondroitin sulfate proteoglycan (CSPG) clearance from a processed nerve graft tissue sample. The method includes the steps of receiving a digital immunohistochemistry (IHC)-stained image of a nerve graft tissue, wherein, the IHC-stained image comprising at least hematoxylin staining and 3,3'-Diaminobenzidine (DAB) staining; generating a digital RGB color image of one or more selected regions of the stained image using an image conversion algorithm; performing, using an image analysis algorithm, a color deconvolution on the one or more selected regions to thereby separate image colors into a hematoxylin image channel, a DAB image channel, and a residual image channel; analyzing pixel intensity values of the image colors of one or more of the image channels based, at least in part, on image processing parameters to determine a number of pixels in one or more of a positive staining region, a negative staining region, and an unstained region in each image channel; and quantifying at least a proportion of the number of pixels analyzed as DAB positive-stained pixels in the positive staining region and DAB negative-stained pixels in the negative stained region in relation to a total number of pixels analyzed to thereby determine CSPG clearance in the processed nerve graft tissue sample.

As illustrated in FIG. 1, the automated method 100 for assessing chondroitin sulfate proteoglycan (CSPG) clearance from a processed nerve graft tissue sample includes receiving 101 a digital immunohistochemistry (IHC)-stained image of a nerve graft tissue. The IHC-stained image may include at least hematoxylin staining and 3,3'-Diaminobenzidine (DAB) staining.

While the following description provides exemplary methods of the present invention for use on peripheral nerve tissue, it should be noted that methods of the present invention may be used on nerve tissue in general, which may include, for example, tissue from the central nervous system (CNS) or tissue from the peripheral nervous system (PNS). Furthermore, the tissue suitable for processing according to the methods herein may be natural or synthetic. For example, the tissue may be soft biological tissue obtained from an animal, such as a mammal, including a human or a non-human mammal (such as but not limited to a pig, monkey, or rodent), or a non-mammal, including a fish, reptile, amphibian, or insect. The tissue may be plant tissue. The graft may be allogeneic or xenogeneic to a patient into which the graft is implanted.

For example, in some embodiments, the nerve graft tissue may be processed peripheral nerve graft tissue that includes decellularized and sterile ECM processed from human peripheral nerve tissue having undergone an enzyme treatment step which cleaves sulfated sugar side chains from a CSPG protein, wherein the immunohistochemistry staining is used to stain chondroitin sulfate side chains a brown color through a DAB immunoperoxidase reaction, and wherein evaluation of CSPG clearance is used for quality control testing for a processed nerve graft tissue production lot. In non-limiting examples, the sulfated sugar side chains may be one or more of chondroitin 4-sulfate, chondroitin 6-sulfate, and dermatan sulfate. As discussed in more detail herein, in some embodiments, a lot average percent negative DAB staining establishes an acceptance criteria for the production lot of processed nerve graft tissue.

Further, the methods include generating 103 a digital RGB color image of one or more selected regions of the stained image using an image conversion algorithm, performing 105, using an image analysis algorithm, image processing techniques such as color deconvolution on the one or more selected regions to thereby digitally separate stains such as hematoxylin and DAB from a color image. The image processing techniques may include a performing a color deconvolution on the one or more selected regions to thereby separate image colors into a hematoxylin image channel, a DAB image channel, and a residual image channel. The method further includes analyzing 107 pixel intensity values of the image colors of one or more of the image channels based, at least in part, on image processing parameters to determine a number of pixels in one or more of a positive staining region, a negative staining region, and an unstained region in each image channel, and quantifying 109 at least a proportion of the number of pixels analyzed as DAB positive-stained pixels in the positive staining region and DAB negative-stained pixels in the negative stained region in relation to a total number of pixels analyzed to thereby determine CSPG clearance in the processed nerve graft tissue sample.

Receiving 101 the digital IHC-stained image(s) may include receiving samples that were histologically processed, sectioned, stained, scanned, and evaluated. The method may include extracting the image for each slide image file. The slide image file may be an SVS file type. Prior to image analysis via methods of the invention, each tissue section may be extracted from the original SVS file type slide.

Figure 2A:
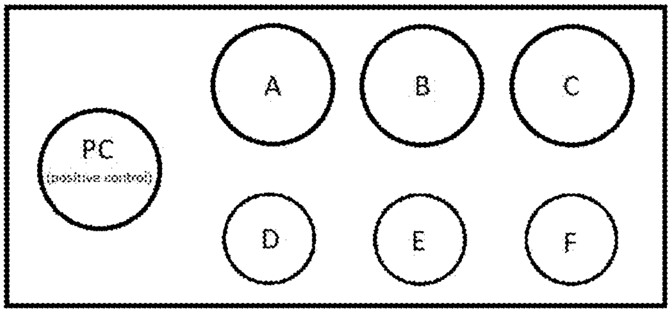
FIG. 2A illustrates a line drawing of an IHC-stained slide according to one embodiment, in which the slide image includes one positive control section and six processed tissue sections.

FIG. 2A illustrates a line drawing of an IHC-stained slide according to one embodiment, in which the slide image includes one positive control section and six processed tissue sections. The six processed tissue sections may be, for example, three sections of large diameter nerve grafts and three sections of small diameter nerve grafts. The large diameter sections may be of nerve grafts that are >3 mm in diameter. The small diameter sections may be of nerve grafts that are <3 mm in diameter. The processed tissue sections may be analyzed for acceptable staining before proceeding with analysis via methods of the invention.

The digital IHC-stained images received 101 may be seamless true color slide images, for example, from an Aperio AT2 Digital Whole Slide Scanner. A digital slide image may be of a whole stained slide created by a whole slide scanner.

a. Image Extraction

Before extraction, the digital slide image of the processed tissue sections are evaluated for acceptability before proceeding with extraction. The evaluation process may be automated, for example performed via one or more algorithms that analyzes quality parameters such as, in non-limiting examples, the number of slide images contained within the digital slide image (i.e. three large diameter product samples, three small diameter product samples, and one unprocessed tissue sample), the type of tissue to be evaluated (i.e. nerve tissue), the quantity of sample contained on the slide (i.e. at least 50%), the presence/absence of any artifacts, and the quality of the focus of the digital slide image. The evaluation process may be a manual process.

Once the digital slide image quality evaluation is complete, regions to be extracted are selected. The extraction process includes ensuring that the amount of background area is minimized. In some embodiments, the regions to be extracted are automatically selected via the one or more algorithms. In some embodiments, the regions to be extracted are selected manually. For extraction, regions to be extracted are selected.

Typically, the entire sample area of the slide image may be extracted. In cases where the sample contains slide debris, shadows, or DAB particulate, the image extraction may be performed such that the affected areas are excluded, and the maximum possible area of the sample is included.

Figure 2B:
FIG. 2B illustrates an example of a whole slide digital image that may be extracted.

FIG. 2B illustrates an example of a whole slide digital image that may be extracted.

Figure 2C:
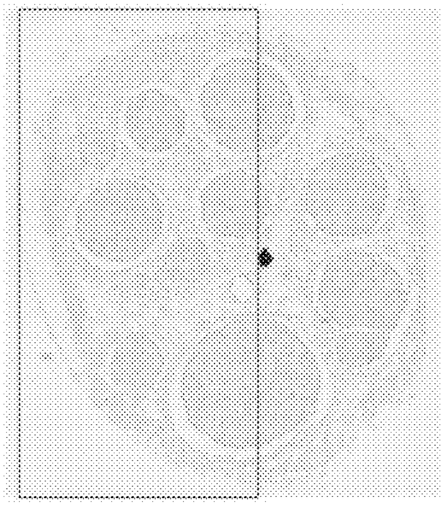
FIG. 2C illustrates an individual region of the digital slide image of the processed nerve graft tissue sample that may be extracted from the whole slide image in the case where the slide contains debris.

FIG. 2C illustrates an individual region of the digital slide image of the processed nerve graft tissue sample that may be extracted from the whole slide image in the case where the slide contains debris. The red rectangle represents the area that may be extracted. Where an individual region of the digital slide image is extracted, the extracted region includes a minimum of 50% of the sample area.

The extracted image(s) may be saved as a TIF file for further analysis. The extracted images may be received 101 as TIF images according to some embodiments of the method. In some embodiments, the digital IHC-stained image is an extracted image in an uncompressed TIF file type of each individual sample extracted from a whole slide scan. In some embodiments, all nerve graft tissue samples on a slide are extracted.

b. Generating Digital RGB Color Images

Figure 3:
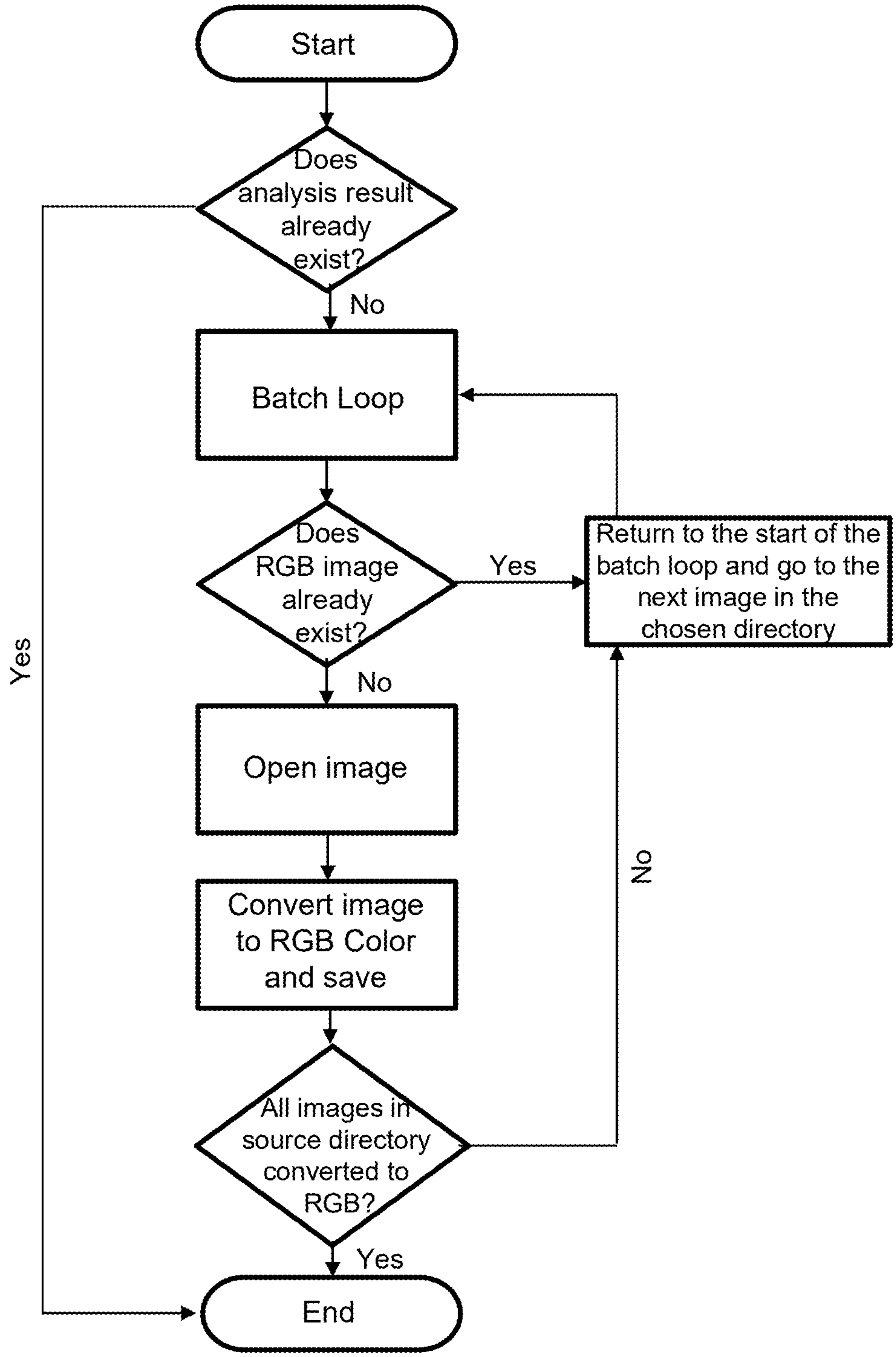
FIG. 3 illustrates a workflow of RGB image conversion according to one embodiment of the invention.

FIG. 3 illustrates a workflow of Red-Green-Blue (RGB) image conversion according to one embodiment of the invention. RGB conversion may be run on an open source platform such as FIJI/ImageJ version 1.49. RGB image conversion may be performed for a batch of images for increased efficiency. Generating 103 a digital RGB image of a selected region may include converting extracted TIF image files such that the image used for image analysis in embodiments of the method is a background corrected, brightfield image in RGB format.

Figure 4A:
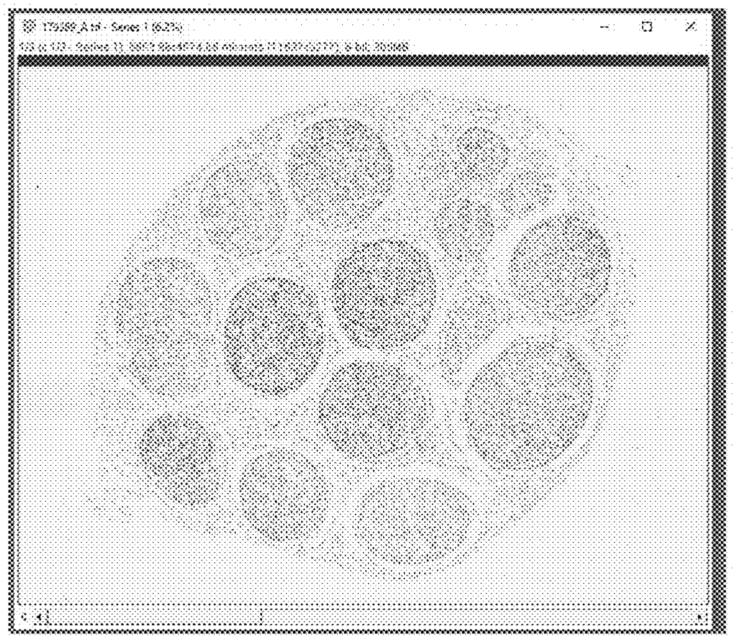
FIG. 4A shows a digital slide image undergoing RGB image conversion.

FIG. 4A shows a digital slide image undergoing RGB image conversion.

Figure 4B:
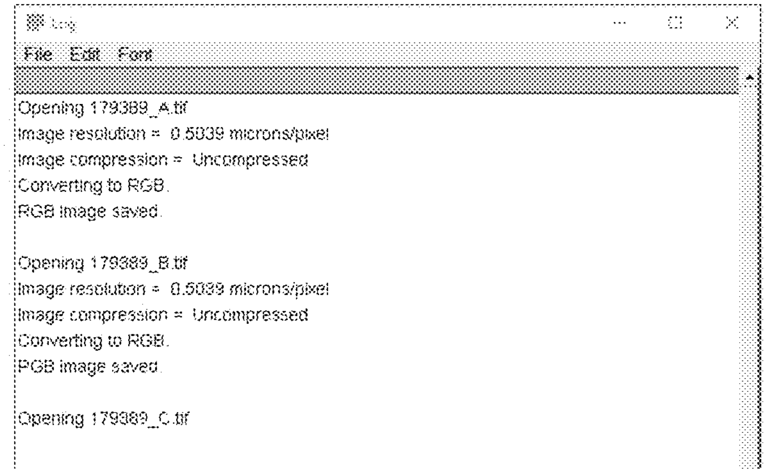
FIG. 4B shows the RGB converter Log Window showing progress and metadata.

FIG. 4B shows the RGB converter Log Window showing progress and metadata. In some embodiments, the generated digital RGB image is saved in a source file/directory further accessed by the image analysis algorithm for analysis. In some embodiments, metadata from the image is displayed during the RGB conversion process to monitor the process. The image resolution and compression information may be obtained from the image metadata and reported in the final data output. In some embodiments, the algorithm converts files in a folder that has partially been converted to RGB and notifies a user if an RGB image already exists for a given TIF file.

Once all files have been converted to RGB, a message in the Log window indicates completion. Converted files saved in the source file (i.e. subfolder) are reviewed to verify that all extracted images were successfully converted. In some embodiments, the review is performed by one or more algorithms. In some embodiments, the review is performed manually by a technician.

c. Performing Image Analysis (Color Deconvolution)

Performing 105, using an image analysis algorithm, image processing techniques on the one or more selected regions to thereby digitally separate stains such as hematoxylin and DAB from a color image may include using an image analysis algorithm developed for color deconvolution. Thus, performing 105 a color deconvolution of the selected regions includes using an image analysis algorithm developed for color deconvolution of IHC-stained digital images of processed nerve graft tissue. The color deconvolution unmixes brightfield images into three image channels representing the absorbance of up to three contributing individual stains. This allows for the separation of, for example, a counterstain such as hematoxylin (which provides non-specific staining for CSPGs but rather is used as a background for unstained tissue visualization) from DAB stain which directly binds to antigen-antibody complexes specific to CSPGs localization in the tissue. This separation is critical when using histological image analysis to provide process quality control during the manufacture of the processed nerve graft tissue.

The image analysis algorithm opens each RGB image saved in the subfolder and performs color deconvolution and image histogram analysis. The RGB image is separated into three image channels.

In the methods for CSPG image analysis disclosed herein, the color deconvolution process produces three image channels. Channel 1 may be the Hematoxylin Image Channel, which is the image produced after color deconvolution that represents the hematoxylin staining in the original hematoxylin and DAB-stained image. The color deconvolution process may subtract the DAB staining from the original image. Channel 2 may be the DAB Image Channel, which is the image produced after color deconvolution that represents the DAB staining in the original hematoxylin and DAB-stained image. The color deconvolution process may subtract the hematoxylin staining from the original image. Channel 3 may be the Residual Image Channel, which may be the image produced after color deconvolution that represents the residual of the color deconvolution process as there is no third dye in the CSPG staining method. In some embodiments, only specific CSPG side chains that inhibit axonal growth are stained.

Figure 5:
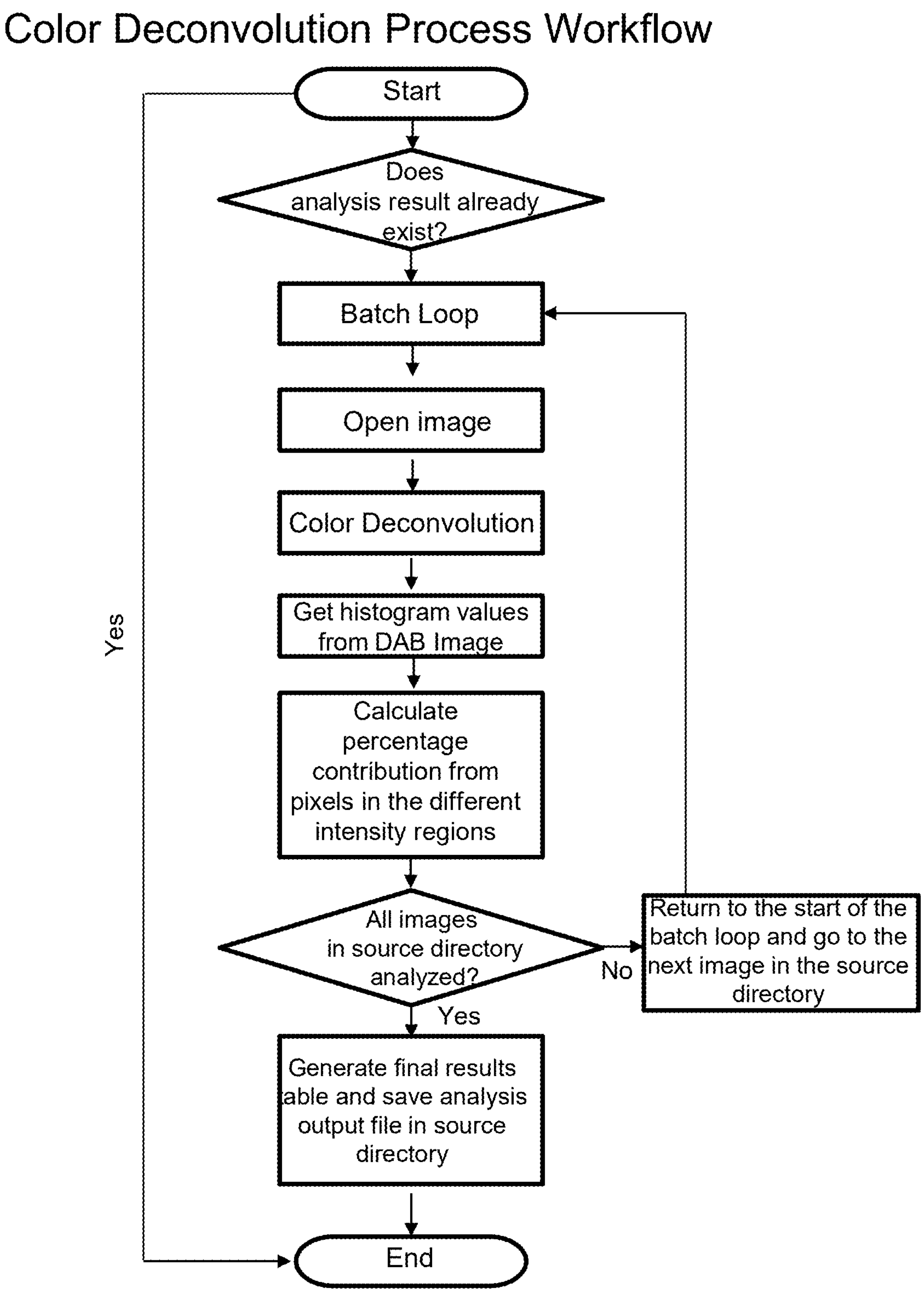
FIG. 5 illustrates performing a color deconvolution and image analysis process workflow according to one embodiment of the invention.

FIG. 5 illustrates performing 105 a color deconvolution and image analysis process workflow according to one embodiment of the invention. The converted RGB image is obtained, and color deconvolution is performed. As described in more detail below, the histogram values from the DAB image channel are obtained and the percentage contribution from pixels in the different intensity regions are calculated. Results are returned in a table as output with the calculations and metadata and stored in the source directory.

In some embodiments of the method, for the hematoxylin image channel, the image produced represents the hematoxylin staining in the IHC-stained image, and wherein the color deconvolution step subtracts the DAB staining from the IHC-stained image. In some embodiments of the method, for the DAB image channel, the image produced after the color deconvolution step represents the DAB staining in the IHC-stained image, and wherein the color deconvolution step subtracts the hematoxylin staining from the IHC-stained image. In some embodiments of the method, for the residual image channel, the image produced after the color deconvolution step represents the residual of the color deconvolution process. In IHC-staining comprising only two stains, the third image channel will be as close to blank as possible.

d. Analyzing Pixel Intensity

Analyzing 107 pixel intensity values of the image colors of one or more of the image channels, may be based, at least in part, on image processing parameters to determine a number of pixels in one or more of a positive staining region, a negative staining region, and an unstained region in each image channel. In some embodiments, the colors in each pixel are analyzed and pixel intensities are quantified.

In some embodiments, the image analysis algorithm includes staining vectors determined from single-dye stained sections of processed and unprocessed nerve graft tissue to ensure accurate stain separation in the color deconvolution process and to identify positive/negative staining pixel intensities for use with the method. Thus, analysis of stain separation is optimized using the determined staining vectors.

In some embodiments, the image processing parameters are determined via analysis of a library of images that include single CSPG-stained sections of peripheral nerve graft samples. The analysis of the library of single CSPG-stained sections of peripheral nerve graft tissue samples may determine an optimal separation of image colors in the color deconvolution process and a range of pixel intensity values for image analysis. For example, In some embodiments, the image processing parameters comprise optimized staining vectors comprising a three-color vector matrix representing red, green, and blue absorbances in a saturated region of each individual image channel, wherein the optimized staining vectors optimize the method for application to processed nerve graft tissue.

Figure 6:
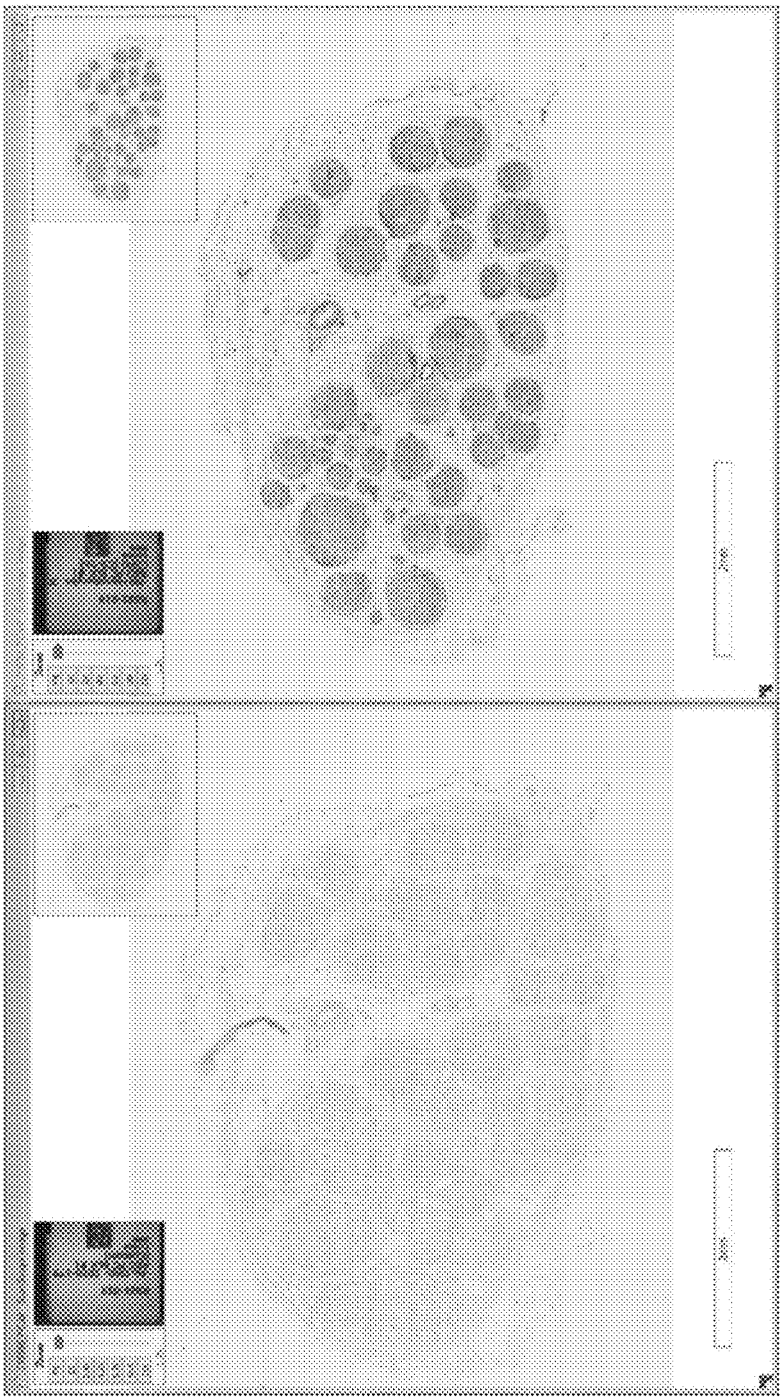
FIG. 6 is a snapshot of the extracted images used for staining vector determination.

FIG. 6 is a snapshot of the extracted images used for staining vector determination. The left panel represents the hematoxylin-only stained image. The right panel represents the DAB-only stained image.

Figure 7:
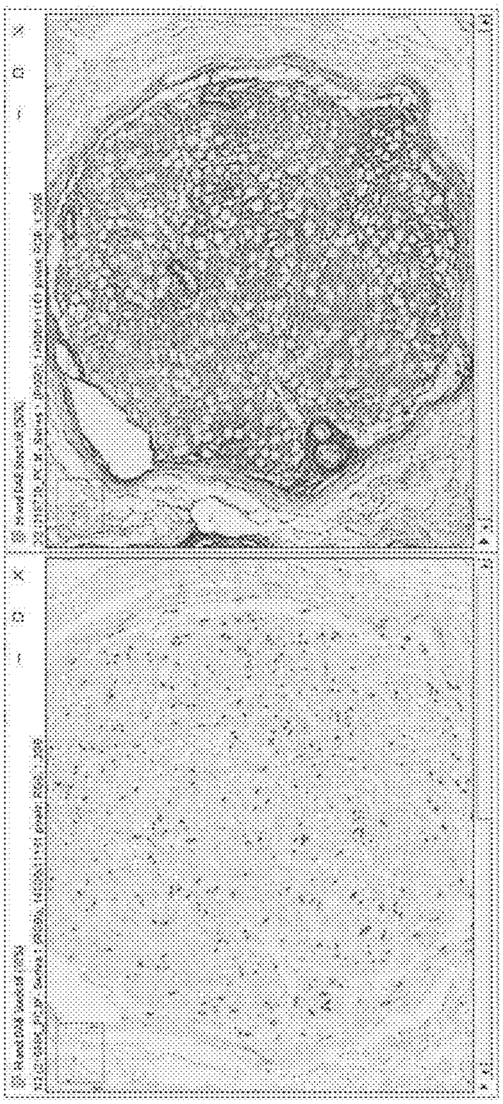
FIG. 7 shows a magnified view of the extracted images used for staining vector determination.

FIG. 7 shows a magnified view of the extracted images used for staining vector determination. The left panel shows the hematoxylin-only staining. The right panel shows the DAB-only staining. In particular, single-dye stained slide images of processed nerve graft tissue samples are obtained and the unprocessed tissue section from the hematoxylin-only slide image and the DAB-only slide image are extracted and converted to RGB image type. The images are further combined into a single image stack, meaning the images opened in a single image window for viewing.

Figure 8:
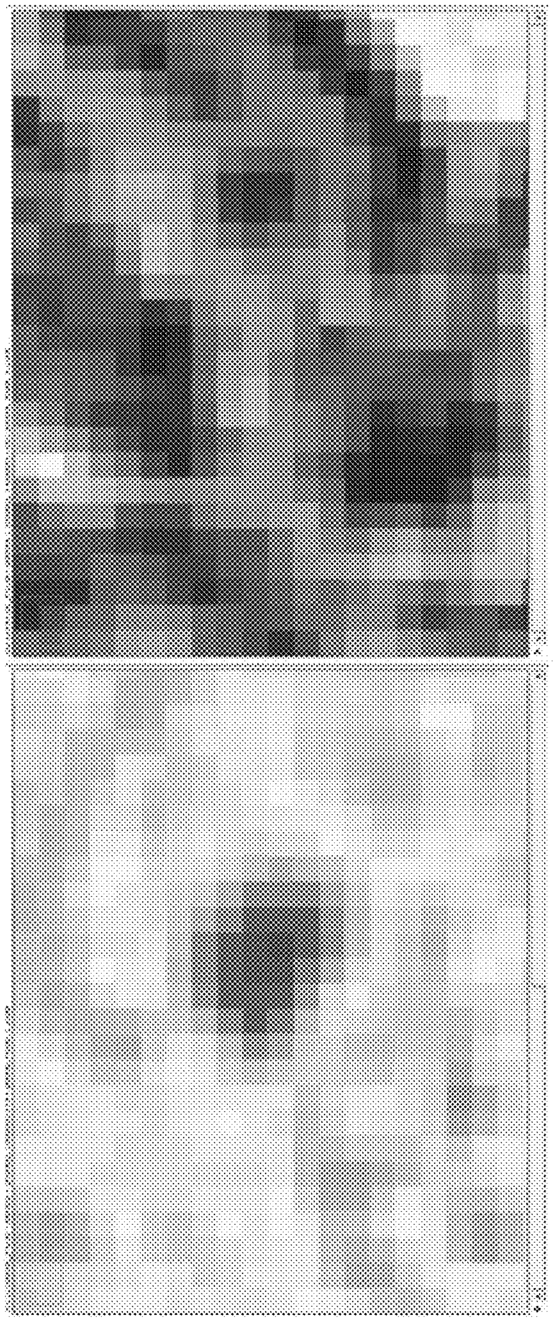
FIG. 8 shows images zoomed to a pixel level to analyze stain intensity and define scoring ranges for determining positive and negative staining for each stain.

As illustrated in FIG. 8, multiple images, used as training data, are zoomed to a pixel level to analyze stain intensity and define scoring ranges for determining positive and negative staining for each stain. Saturated pixels, i.e. strong staining, are identified for each image. Small areas, for example between 4 and 12 pixels, containing only pixels saturated with the stain color and without any unstained or low intensity areas are selected and analyzed. In some embodiments, the pixel intensities of a plurality of different CSPG stained samples are analyzed. The pixels are analyzed for all possible staining to define the pixel intensity value range criteria used in the methods of the invention. The algorithm calculates the color deconvolution parameters based on the staining vectors determined from the images analyzed. Further, the calculated staining vectors are used to perform color deconvolution on a set of positive control test images to evaluate stain separation accuracy of the algorithm. The process of determining pixel level stain intensities from training data is repeated until optimized staining vectors are determined.

Thus, the image analysis algorithm is used to analyze pixel intensity values of the image colors and quantify a proportion of a sample that is positive and negatively stained for the chromogen, for example, DAB. As discussed in more detail herein, the automated methods for image analysis provide a direct measure of DAB staining, which directly correlates to the presence of CSPG in the sample.

In some embodiments, the methods include analysis of a reference standard of reference image. The reference standard (also referred to as the reference image) may be an image that has been previously analyzed and the image analysis results are known. It is intended to verify the repeatability of the method each time the analysis is performed. A current reference image data are provided for comparison to ensure the accuracy of the automated methods.

For the digital slide images, a pixel intensity value may be represented as an integer that ranges from 0 to 255. The image pixel count may be the total number of pixels in the image. In digital image analysis, the pixel intensity values for any color range from 0 to 255, wherein 0 represents the darkest shade of color and 255 represents the lightest shade of color as standard. During image analysis 107, the pixel intensity values in each image channel are analyzed for any color in the range of from 0 to 255 inclusive. A pixel intensity value of 0 may be black, while a pixel intensity value of 255 may be white. The image analysis algorithms of methods of the invention analyze the individual pixel intensities of a digital image. Thus, in some embodiments, a pixel intensity value of 0 represents a darkest shade of color and a pixel intensity value of 255 represents a lightest shade of color. In some embodiments, the pixel intensity value may be represented by a pixel absorbance value. For example, the pixel intensity value may be converted to absorbance.

In some embodiments, the total pixels analyzed includes the number of pixel intensity values between 0 and 235 inclusive analyzed. However, it is noted that the total pixels analyzed may include the number of pixel intensity values in any range that encapsulates the color range of the stains used in the IHC-staining process.

e. Quantifying Positive-Stained/Negative-Stained Regions

The methods include quantifying 109 at least a proportion of the number of pixels analyzed as DAB positive-stained pixels in the positive staining region and DAB negative-stained pixels in the negative stained region in relation to a total number of pixels analyzed to thereby determine CSPG clearance in the processed nerve graft tissue sample. For example, the proportion of pixels that are positive (0 to 180 intensity range) and negative (181 to 235 intensity range) for DAB staining may be determined. Pixels that are unstained areas or glass (intensity range between 236 to 255) are excluded from analysis.

Particular to IHC staining for CSPG analysis, in some embodiments, the positive staining regions comprise pixel intensity values between 0 and 180 inclusive. In some embodiments, the negative staining regions include pixel intensity values between 181 and 235 inclusive. The unstained regions include pixels between 236 and 255 inclusive intensity values, in some embodiments. In unstained regions, the pixels represent absence of extracellular matrix (ECM) tissue and are excluded from the analysis, in some embodiments.

Accordingly, in some embodiments, the percent (%) DAB positive-stained pixels is the proportion of pixels in the DAB image channel having an intensity value between 0 and 180 inclusive that represent positive DAB staining as compared to the total pixels analyzed, represented by equation (I) below:

$$\text{Positive } DAB \text{ Staining} = \left(\frac{\text{number of pixels in the range of 0–180 intensity value}}{\text{number of pixels in the range of 0–235 intensity value}}\right) \times 100 \tag{I}$$

In some embodiments of the methods, the percent negative DAB staining is the proportion of pixel intensity values in the DAB image channel with intensity value between 181 and 235 inclusive that represent negative DAB staining as compared to the total pixels analyzed, represented by equation (II) below:

$$\text{Negative } DAB \text{ Staining} = \left(\frac{\text{number of pixels in the range of 181–235 intensity value}}{\text{number of pixels in the range of 0–235 intensity value}}\right) \times 100 \tag{II}$$

In some embodiments, only the DAB channel images are analyzed for positive- and negative-stained pixels. The automated image analysis method provides a direct measure of sample area that is negative for DAB staining, which directly correlates to the presence of CSPG in the sample. Thus, the image analysis determines the number of pixels in the DAB image (Image channel 2 after color deconvolution of the RGB image) that are positive for DAB staining (intensity range of 0-180) and negative for DAB staining (intensity range of 181-235). Pixels that are unstained areas or glass (intensity range between 236 to 255) are excluded from analysis.

In some embodiments, the calculated percent of DAB negative-stained pixels correlates to removal of CSPG in the processed nerve graft tissue sample. In some embodiments, the calculated percent of DAB positive-stained pixels correlates to the presence of CSPG in the processed nerve graft tissue sample.

Figure 9A:
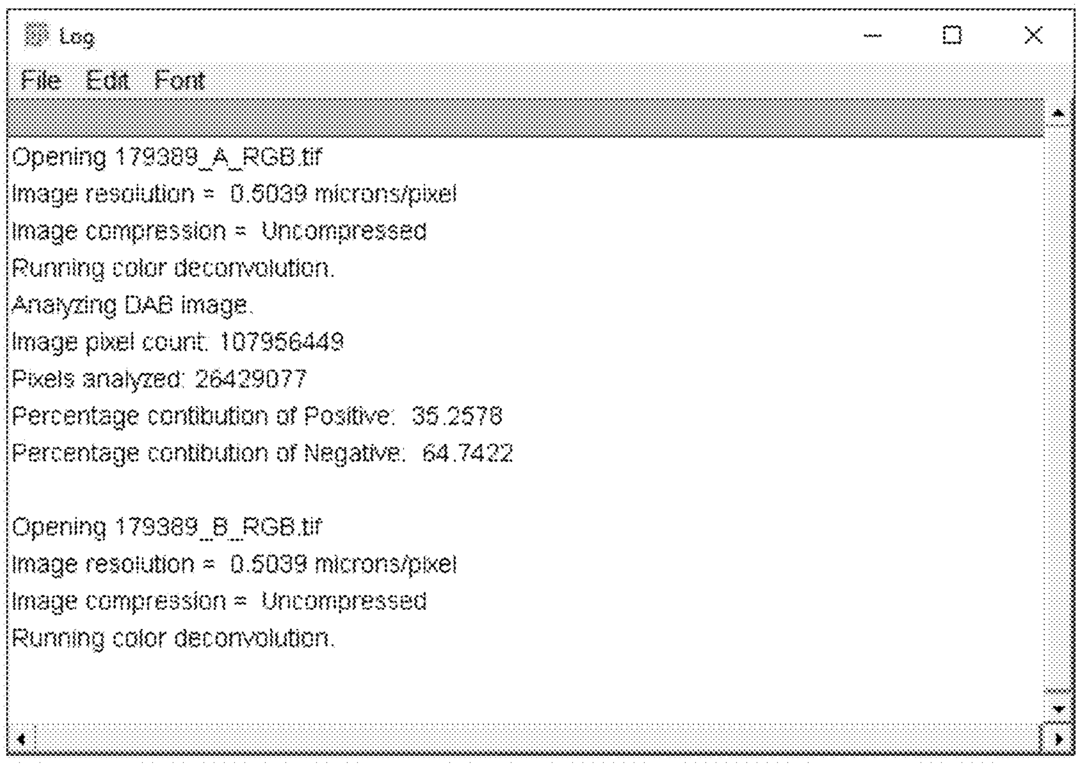
FIG. 9A shows the Log window used to show progress as the image histogram is analyzed and the percent contribution of pixels that are positive and negative for DAB staining based on the pixel intensity values are calculated.

FIG. 9A shows the Log window used to show progress as the image histogram is analyzed and the percent contribution of pixels that are positive and negative for DAB staining based on the pixel intensity values are calculated.

FIG. 9B shows an output format of the calculated image information. The output may include the image ID of the RGB image, the image compression of the RGB image, the image resolution of the RGB image, the image pixel count of the DAB image (Image channel 2 after color deconvolution of the RGB image), number of pixels analyzed in the DAB image (i.e., number of pixels between 0-235 intensity range), percentage of pixels positive for DAB staining (i.e., ratio of pixels between 0-180 and 0-235), and percentage of pixels negative for DAB staining (i.e., ratio of pixels between 181-235 and 0-235). Additionally, the image analysis algorithm may include Image Compression and Image Resolution as part of the data output file. This allows for verification that the image extraction process was performed correctly for each image by verification of the image resolution and compression type.

Figure 10B:
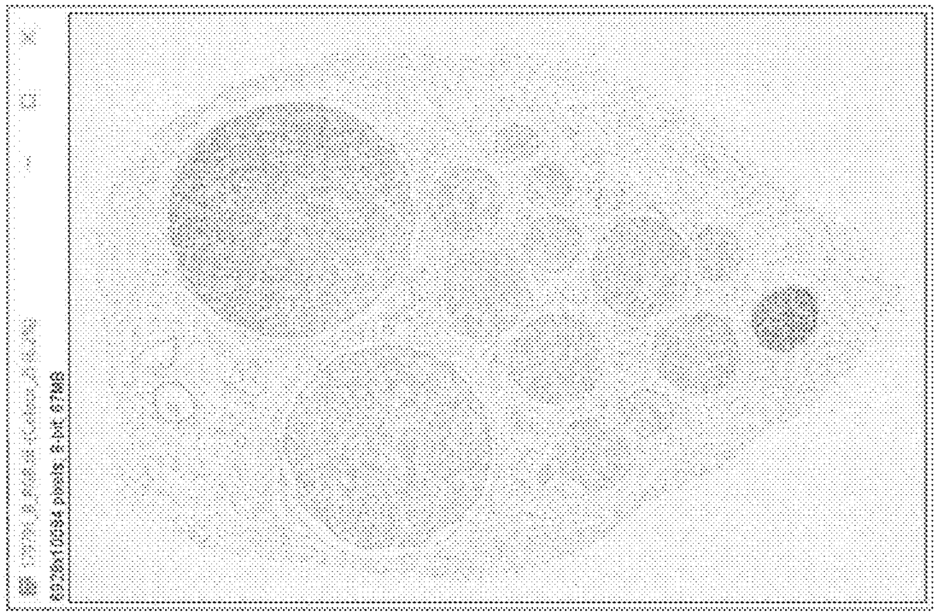
FIGS. 10A and 10B show an example of the color deconvolution and image analysis process.
Figure 10A:
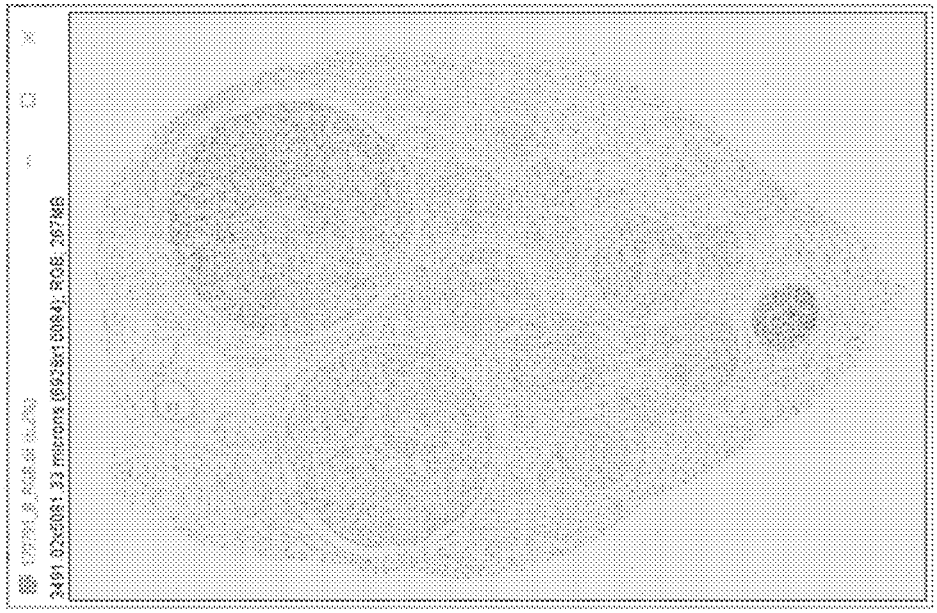

FIGS. 10A and 10B show an example of the color deconvolution and image analysis process. FIG. 10A shows the original RGB image of hematoxylin and DAB staining. FIG. 10B shows the DAB image after color deconvolution. The hematoxylin stain contribution has been subtracted from the original image.

Figure 11:
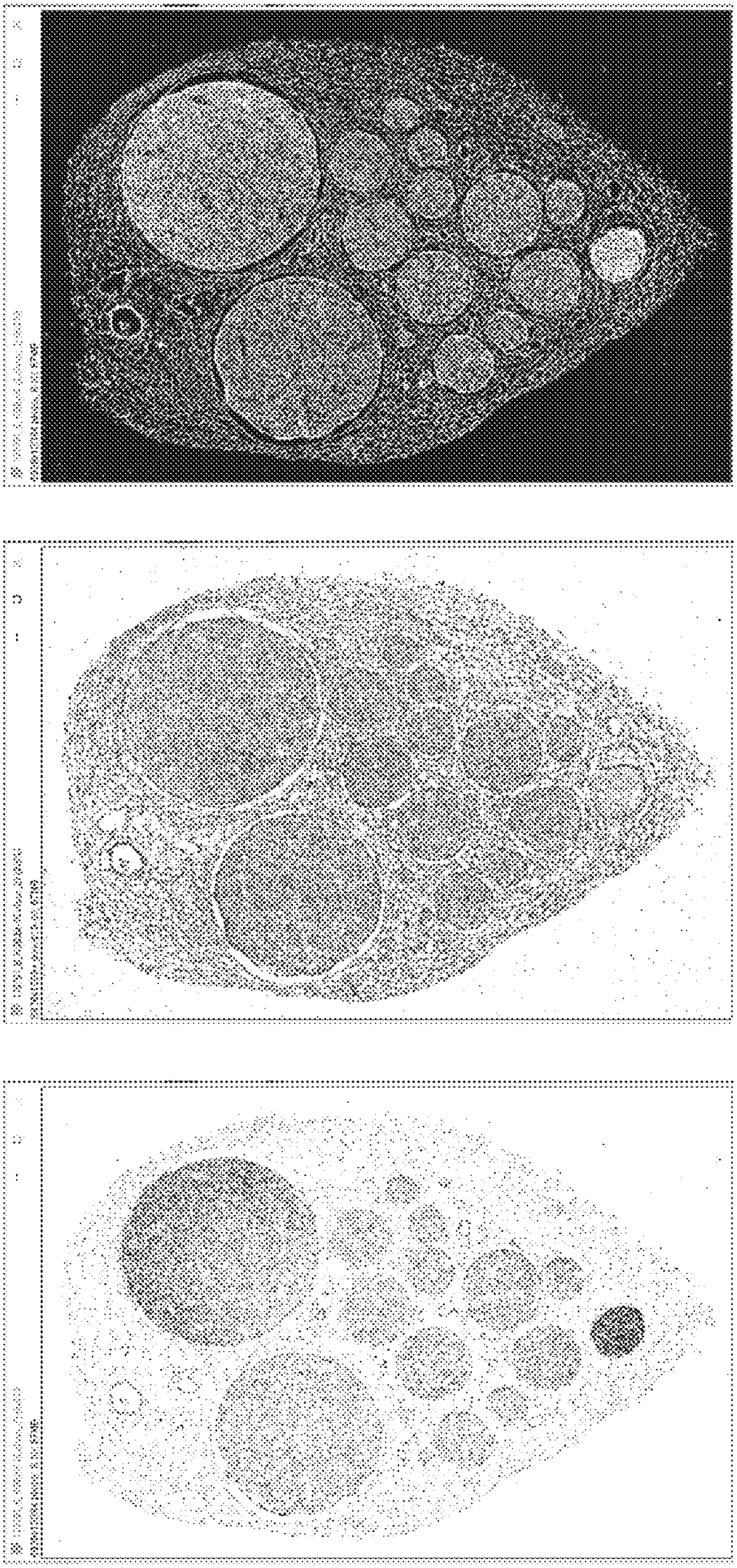
FIG. 11 illustrates color deconvolution and image analysis of the DAB staining channel. Panel A shows positive DAB staining represented by black pixels. Panel B shows negative DAB staining represented by black pixels. Channel C shows unstained areas represented by black pixels.

FIG. 11 illustrates color deconvolution and image analysis of the DAB staining channel. Panel A shows positive DAB staining represented by black pixels. Panel B shows negative DAB staining represented by black pixels. Channel C shows unstained areas represented by black pixels.

Methods for Analyzing Lot Average CSPG Clearance Score/Batch Quality Control

Clearance of CSPG in processed nerve graft tissue may be a product quality attribute for the manufactured product. The Lot Average CSPG Clearance Score may be defined as the average level of CSPG clearance in the processed nerve graft tissue samples. The Lot Average Clearance may be represented as the average proportion of negative DAB staining (%) in the processed nerve graft tissue samples. In this way, evaluating the average level of CSPG clearance in the processed nerve graft tissue sample using the image analysis methods of the invention allows for direct evaluation of CSPG clearance.

As discussed herein, the methods may be applied to any immunostaining method where, for example, DAB is used as a chromogen to identify antigen-antibody reaction and hematoxylin is used as a counterstain. In the case of the peripheral nerve system, the methods may be applied to axon-associated structural proteins such as Neurofilament, alpha- and beta-Tubulins, Actins (F-Actin), GAP-43, Collagen types I, III, IV, V, Fibronectin, Elastin, and myelin related components such as Myelin basic protein, myelin associated glycolipids and proteolipids, sugar side chains, and any other peripheral nerve structural protein or other type of component of interest (proteoglycans, growth factors, etc.).

In some embodiments, the nerve graft tissue may be processed peripheral nerve graft tissue that includes decellularized and sterile ECM processed from human peripheral nerve tissue having undergone an enzyme treatment step which cleaves sulfated sugar side chains from a CSPG protein. Accordingly, the immunohistochemistry staining is used to stain chondroitin sulfate side chains a brown color through a DAB immunoperoxidase reaction. Thus, the evaluation of CSPG clearance may be used for quality control testing for a processed nerve graft tissue production lot.

Figure 12:
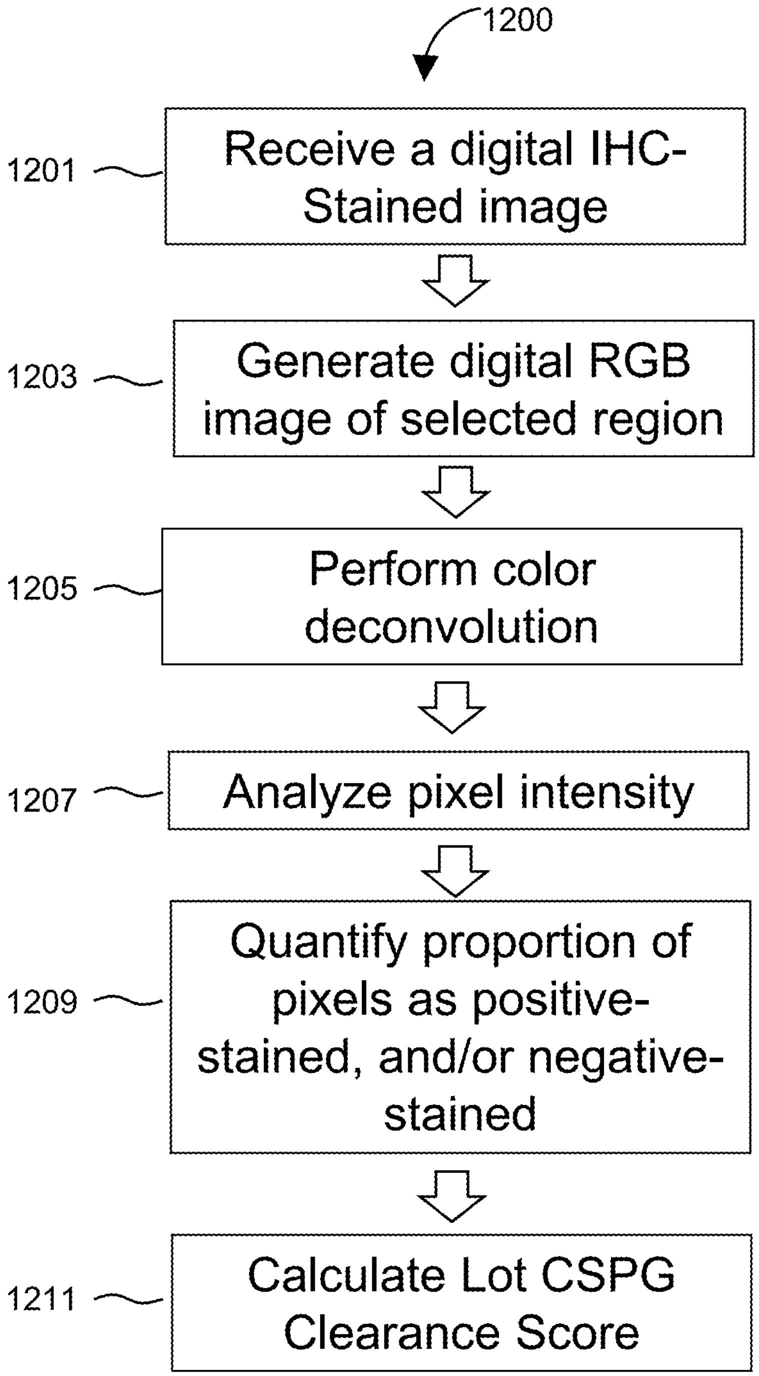
FIG. 12 illustrates an automated method for performing a quality control evaluation of a lot of processed nerve graft tissue.

FIG. 12 illustrates steps of an automated method for performing a quality control evaluation of a lot of processed nerve graft tissue.

The automated method for performing a quality control evaluation 1200 of processed nerve graft tissue for CSPG clearance may include receiving 1201 a digital immunohistochemistry (IHC)-stained image of a nerve graft tissue, wherein, the IHC-stained image comprising at least hematoxylin staining and 3,3'-Diaminobenzidine (DAB) staining; generating 1203 a digital RGB color image of one or more selected regions of the stained image using an image conversion algorithm; performing 1205, using an image analysis algorithm, a color deconvolution on the one or more selected regions to thereby separate image colors into a hematoxylin image channel, a DAB image channel, and a residual image channel; analyzing 1207 pixel intensity values of the image colors of one or more of the image channels based, at least in part, on image processing parameters to determine a number of pixels in one or more of a positive staining region, a negative staining region, and an unstained region in each image channel; quantifying 1209 at least a proportion of the number of pixels analyzed as DAB positive-stained pixels in the positive staining region and DAB negative-stained pixels in the negative stained region in relation to a total number of pixels analyzed; and calculating 1211 a percent clearance for a batch lot of the processed nerve graft tissue.

In some embodiments, the nerve graft tissue is processed peripheral nerve graft tissue that includes decellularized and sterile ECM processed from human peripheral nerve tissue having undergone an enzyme treatment step which cleaves sulfated sugar side chains from a CSPG protein core, wherein the immunohistochemistry staining is used to stain chondroitin sulfate side chains a brown color through a DAB immunoperoxidase reaction. Accordingly, the evaluation of CSPG clearance is used for quality control testing for a processed nerve graft tissue production lot. In non-limiting examples, the sulfated sugar side chains comprise one or more of chondroitin 4-sulfate, chondroitin 6-sulfate, and dermatan sulfate. As discussed in detail herein, a lot average percent negative DAB staining establishes an acceptance criteria for the production lot of processed nerve graft tissue. Further, the method may include batch processing of a plurality of digital IHC-stained images, wherein a batch of images are analyzed at once.

As disclosed herein, the automated image analysis methods of the invention provide a direct measure of DAB staining in processed nerve graft histological samples, which directly correlates to the presence of CSPG in the sample of nerve graft tissue. Using methods of the invention described herein, the acceptance criteria for CSPG clearance may be, in non-limiting examples, ≥71.7% lot average negative DAB staining. An alert range may be defined, in non-limiting examples, as ≥71.7% and <80.0% lot average negative DAB staining.

The samples are received, extracted, converted to RGB, and analyzed according to the methods disclosed herein. The methods include quantifying at least a proportion of the number of pixels analyzed as DAB positive-stained pixels in the positive staining region and DAB negative-stained pixels in the negative stained region in relation to a total number of pixels analyzed and calculating a percent clearance for a batch lot of the processed nerve graft tissue. For example, the proportion of pixels that are positive (0 to 180 intensity range) and negative (181 to 235 intensity range) for DAB staining may be determined. Pixels that are unstained areas or glass (intensity range between 236 to 255) are excluded from analysis.

As disclosed, particular to IHC staining for CSPG analysis, in some embodiments, the positive staining regions comprise pixel intensity values between 0 and 180 inclusive. In some embodiments, the negative staining regions include pixel intensity values between 181 and 235 inclusive. The unstained regions include pixels between 236 and 255 inclusive intensity values, in some embodiments. In unstained regions, the pixels represent absence of extracellular matrix (ECM) tissue and are excluded from the analysis, in some embodiments.

Accordingly, in some embodiments, the percent (%) DAB positive-stained pixels is the proportion of pixels in the DAB image channel having an intensity value between 0 and 180 inclusive that represent positive DAB staining as compared to the total pixels analyzed, represented by equation (I) below:

$$\text{Positive } DAB \text{ Staining} = \left(\frac{\text{number of pixels in the range of 0–180 intensity value}}{\text{number of pixels in the range of 0–235 intensity value}}\right)\times 100 \tag{I}$$

In some embodiments of the methods, the percent negative DAB staining is the proportion of pixel intensity values in the DAB image channel with intensity value between 181 and 235 inclusive that represent negative DAB staining as compared to the total pixels analyzed, represented by equation (II) below:

$$\text{Negative } DAB \text{ Staining} = \left(\frac{\text{number of pixels in the range of 181–235 intensity value}}{\text{number of pixels in the range of 0–235 intensity value}}\right)\times 100 \tag{II}$$

In some embodiments, only the DAB channel images are analyzed for positive- and negative-stained pixels. The automated image analysis method provides a direct measure of sample area that is negative for DAB staining, which directly correlates to the presence of CSPG in the sample of nerve graft tissue. Thus, the image analysis determines the number of pixels in the DAB image (Image channel 2 after color deconvolution of the RGB image) that are positive for DAB staining (intensity range of 0-180) and negative for DAB staining (intensity range of 181-235). Pixels that are unstained areas or glass (intensity range between 236 to 255) are excluded from analysis.

In some embodiments, the calculated percent of DAB negative-stained pixels correlates to removal of CSPG in the processed nerve graft tissue sample. In some embodiments, the calculated percent of DAB positive-stained pixels correlates to the presence of CSPG in the processed nerve graft tissue sample.

Calculation of the Lot Average negative DAB staining (%) may be represented as the average proportion of negative DAB staining (%) in the processed nerve graft tissue samples. Accordingly, the Lot Average negative DAB staining (%) may be compared to defined product specifications.

In some embodiments, the methods include increasing the size of the variable arrays available for processing by the image analysis algorithm to allow for batch analysis of multiple lots of processed nerve graft tissue samples. For example, in some embodiments, the image analysis algorithm may process up to 70 RGB images during a single execution, corresponding to ten lots of nerve grafts (seven images per lot-six processed tissue samples and one positive control).

In some embodiments, only specific CSPG side chains that inhibit axonal growth are stained. Thus, the values of percent negative staining (the proportion of pixels in the negative intensity range) are used to determine the level of CSPG clearance that inhibits axonal growth in the processed nerve graft tissue samples, and to assess the quality of positive control staining. Sample tracing is not necessary with some embodiments of this method, as unstained areas or glass may be automatically excluded from analysis. The method provides for increased sensitivity in detecting deviations from accepted batch Lot CSPG Clearance values.

The methods may also include an IHC staining Positive Control, and an IHC Negative Control. The IHC Positive Control may be a slide that is used during staining to monitor the quality of the staining process. Slides may be taken from a nerve graft histology block that has shown acceptable positive staining in an anti-CSPG IHC staining protocol. The IHC positive control may be automatically evaluated for normal staining, weak staining, and unacceptable staining. Normal staining, i.e. strong brown staining specific to structures that are expected to stain for CSPG (i.e., perineurium, endoneurium and blood vessels) with minimal staining of the surrounding tissues. For example, clear differentiation may be visible between those structures and the surrounding tissues. Unacceptable staining of the positive control may be light to no brown staining and/or lack of differentiation between the endoneurium and the surrounding tissues. Lack of specificity primarily may present as lack of staining of the endoneurium.

The IHC Negative Control may be a slide that is used during staining to determine non-specific staining. Sections are stained using isotype primary antibody non-specific to the target epitope. This slide is also referred to as the isotype control.

As disclosed herein the method may also include a Positive Control for evaluating the efficacy of the automated method. The Positive Control may be a donor-matched unprocessed sample of peripheral nerve tissue.

Example Evaluation of Stain Separation of Automated Method Accuracy

An optimization study was conducted to determine staining vectors and evaluate the automated stain separation and image analysis accuracy of the automated methods of the invention. Staining vectors were determined from single-dye-stained sections of processed nerve graft tissue to ensure accurate stain separation in the color deconvolution process, and to characterize the quality of the processed nerve graft tissue samples using the automated and optimized image analysis method.

Figure 13:
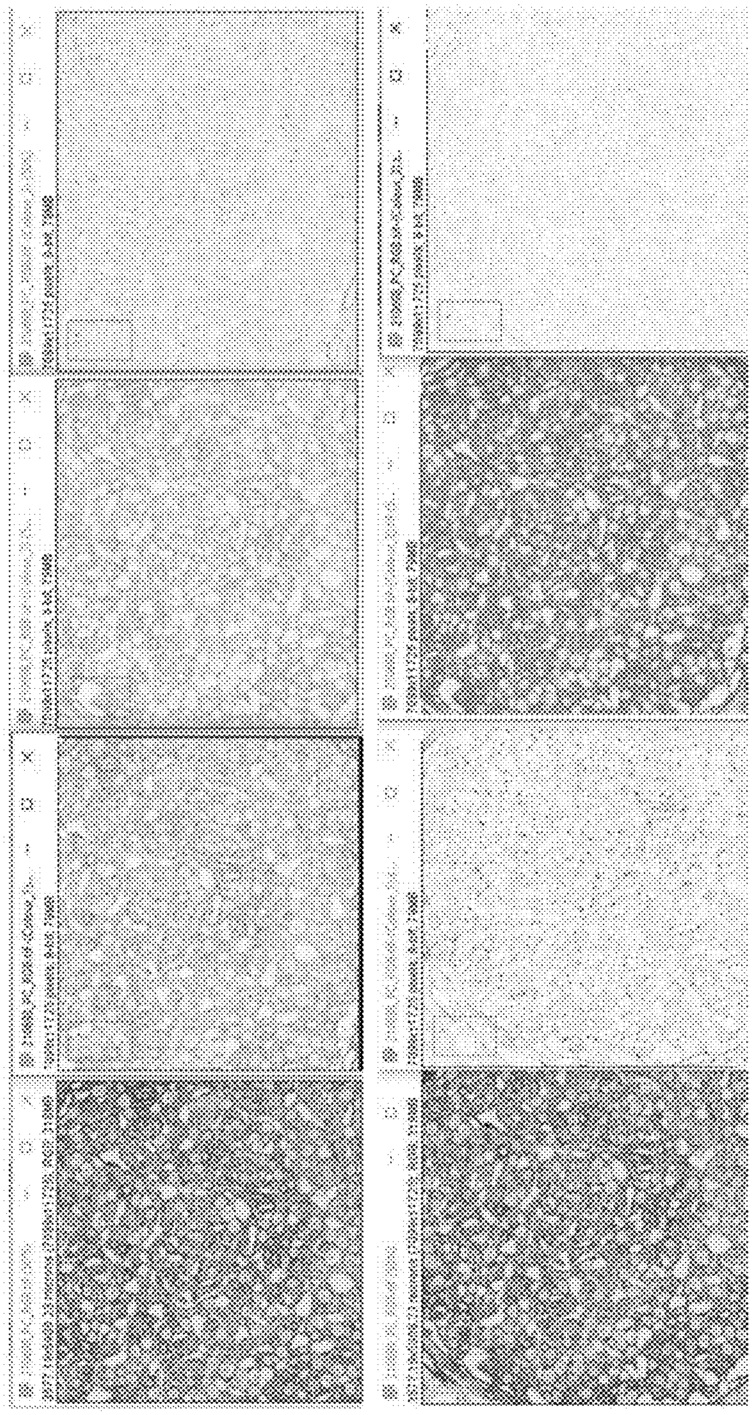
FIG. 13 shows a magnified example of the color deconvolution output. The top row contains the images produced using a set of standard IHC Profiler staining vectors, and the bottom row contains the images produced using the optimized new staining vectors developed for the method.

FIG. 13 shows a magnified example of the color deconvolution output. The top row contains the images produced using a set of standard IHC Profiler staining vectors, and the bottom row contains the images produced using the optimized new staining vectors developed for the method. From left to right, the images are the normal-stained (hematoxylin and DAB) image, the hematoxylin image, the DAB image, and the residual image. As compared to standard staining vectors, the calculated new staining vectors more accurately separate the individual stains in images of processed nerve graft tissue samples. Further, the amount of information in the residual image was minimized with the new staining vectors. Confirmation and evaluation was performed using visual inspection of the image, and by analyzing the image histogram for the proportion of pixels in the intensity range of 236-255.

Results: For Chondroitin Sulfate Proteoglycans (CSPG) (Immunoperoxidase based stains using primary antibodies)-unprocessed tissue stained strongly for CSPG. Processed tissue stained only weakly. The processing included an enzyme step to selectively remove the CSPG. The staining observed with unprocessed and processed tissue within and across a representative set of lots as expected with low levels of staining in processed tissue.

Figure 14:
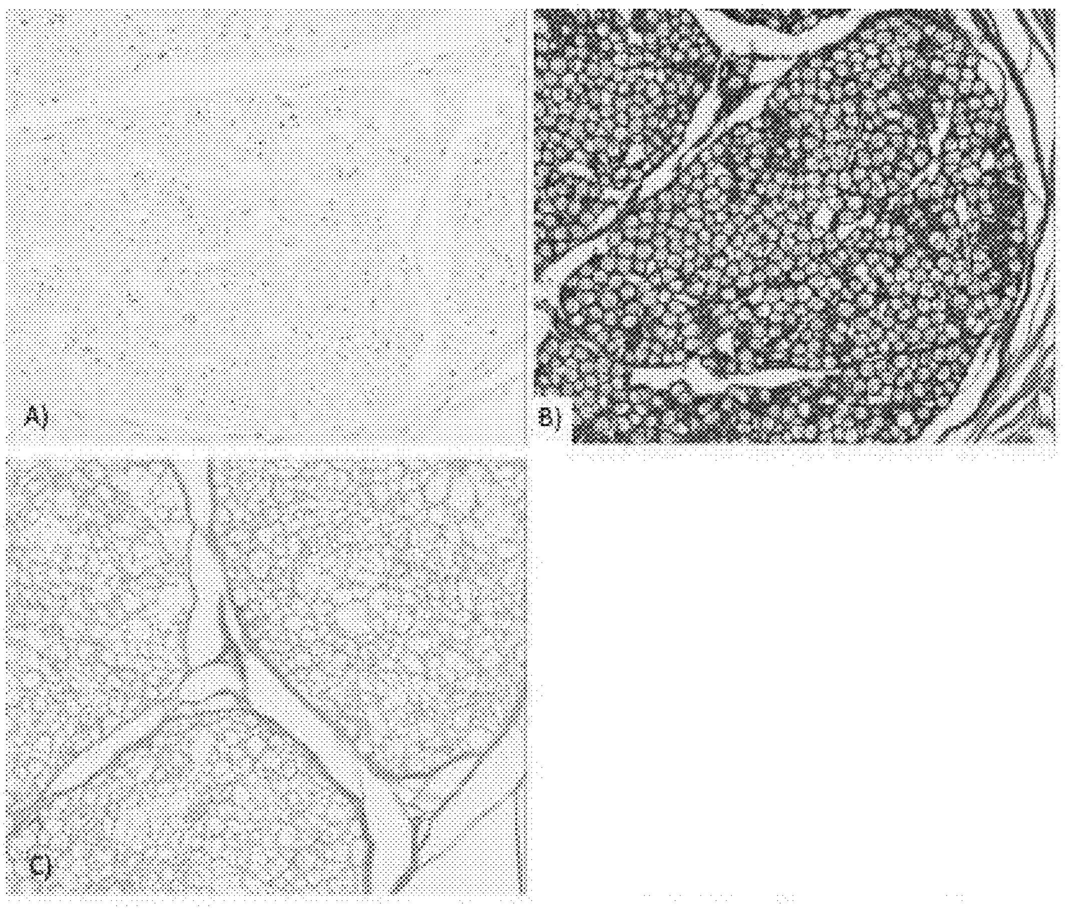
FIG. 14 illustrates representative micrographs of CSPG IHC staining of unprocessed nerve tissue (Panel B), and processed nerve tissue (Panel C). Panel A shows the isotype control (i.e. negative staining control) of unprocessed tissue.

FIG. 14 illustrates representative micrographs of CSPG IHC staining of unprocessed nerve tissue (Panel B), and processed nerve tissue (Panel C). Panel A shows the isotype control (i.e. negative staining control) of unprocessed tissue.

The accuracy of stain separation was evaluated by performing color deconvolution on images of normal-stained (hematoxylin and DAB) nerve graft unprocessed tissue. The color deconvolution output of the new staining vectors was compared to a standard IHC Profiler.

Figure 15A:
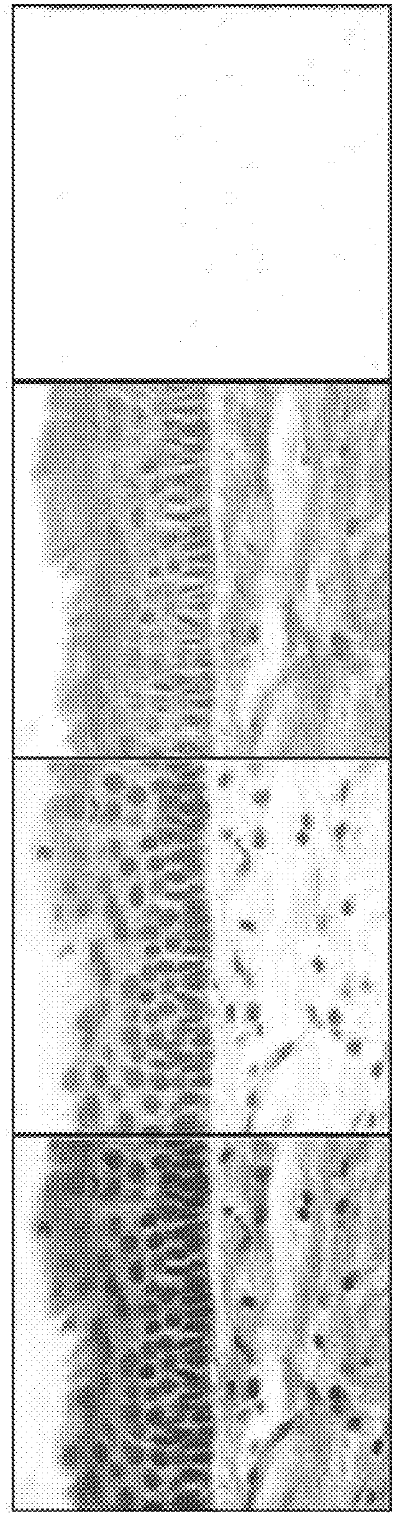
FIGS. 15A and 15B illustrate evaluation of stain separation accuracy using the algorithm(s) of the methods.
Figure 15B:
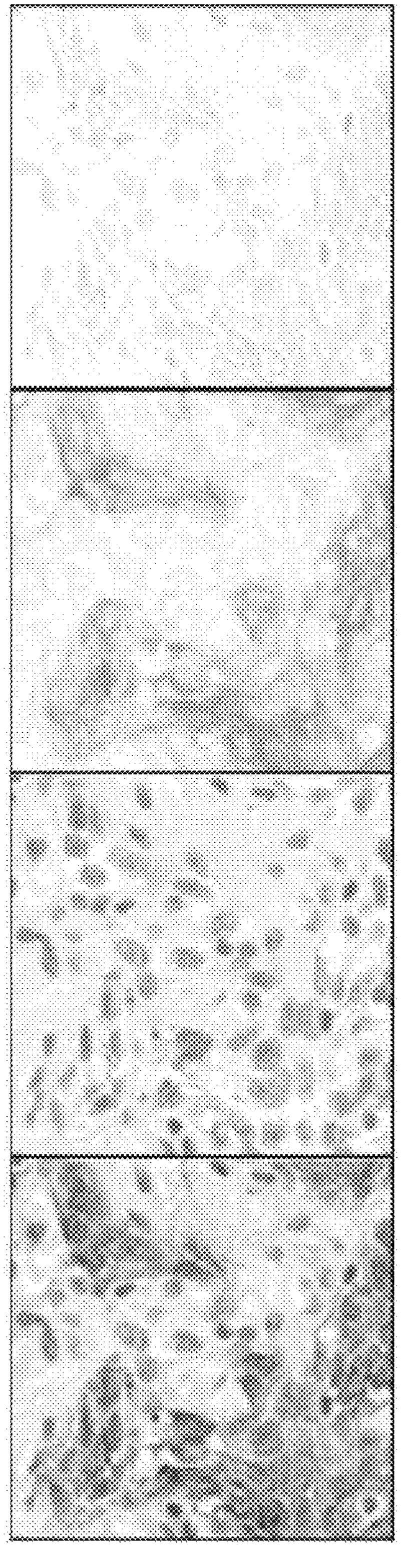

FIGS. 15A and 15B illustrate evaluation of stain separation quality and accuracy using the algorithm(s) of the methods. Tissue samples were characterized using the optimized image analysis methods of the invention. The color deconvolution method separates an image into a set of three images showing the representation of three contributing stains. In a two-dye-stained slide image, the third image channel should be as close to blank as possible. A representative set tissue samples slide images were analyzed using the optimized image analysis methods. FIG. 15A illustrates Hematoxylin and eosin unmixing using the calculated staining vectors. From left to right, the panels show the original image, hematoxylin, eosin, and a virtually empty third (complementary) component. The vectors match the image very well. FIG. 15B illustrates the hematoxylin and DAB unmixing using the calculated staining vectors. From left to right, the panels show the original image, hematoxylin, DAB, and the third component. For this run the vectors did not perfectly match the stains in the image so were re-calculated using the single-stained images as described above.

A representative set of lots were selected for characterization using the optimized image analysis method. The selected samples were manufactured between 2017-2021 and include samples with different variations of staining based on semiquantitative analysis. Stain separation was evaluated by visual inspection based on the guidance provided in reference and by comparison to single-dye-stained unprocessed nerve graft tissue. The following criteria were used: the hematoxylin image should show specific hematoxylin staining of cell nuclei, with minimal background ECM staining; the hematoxylin image should match the single-dye-stained image as much as possible; the DAB image should show specific DAB staining of CSPG-containing structures (e.g., endoneurial tubes and blood vessels), with minimal background ECM staining. The DAB image should match the single-dye-stained image as much as possible. The residual image should be as close to blank as possible.

The Lot Average automated score was calculated for the processed nerve graft lots that passed the semiquantitative criteria (Lot Average CSPG Clearance Score ≥3.50, n=51) and lots that failed the semiquantitative criteria (Lot Average CSPG Clearance Score <3.50, n=2). The automated score was calculated for positive control samples. The positive control samples were divided into acceptable and unacceptable groups based on visual assessment. The assessment of acceptable or unacceptable was based on the semiquantitative method which requires a strong positive staining in order for the sample to be used as the staining comparator for scoring processed tissue. The acceptable group was further subdivided into Normal staining groups and Weak staining groups. The automated score was calculated for IHC negative controls. The IHC negative control can be considered as the blank or background noise for this assay. The data for IHC negative controls were plotted using boxplots and individual value plots. The automated score was then calculated for individual nerve graft tissue samples. The individual samples were subdivided into groups based on sample size and CSPG clearance level. Large and small diameter samples were evaluated to determine if they are statistically different using a two-sample t-test.

The large diameter samples have a higher average negative DAB staining % (86.3±9.8) compared to that of the small diameter grafts (84.6±9.6); however, the difference in mean is not statistically significant (p-value=0.118), and the 95% confidence interval for the mean overlaps between the two groups.

For outlier analysis, the data from passing lots were reviewed to determine a value that indicates that the automated score may be an outlier. For example, this may indicate an abnormal level (i.e., low level) of CSPG clearance.

Figure 16:
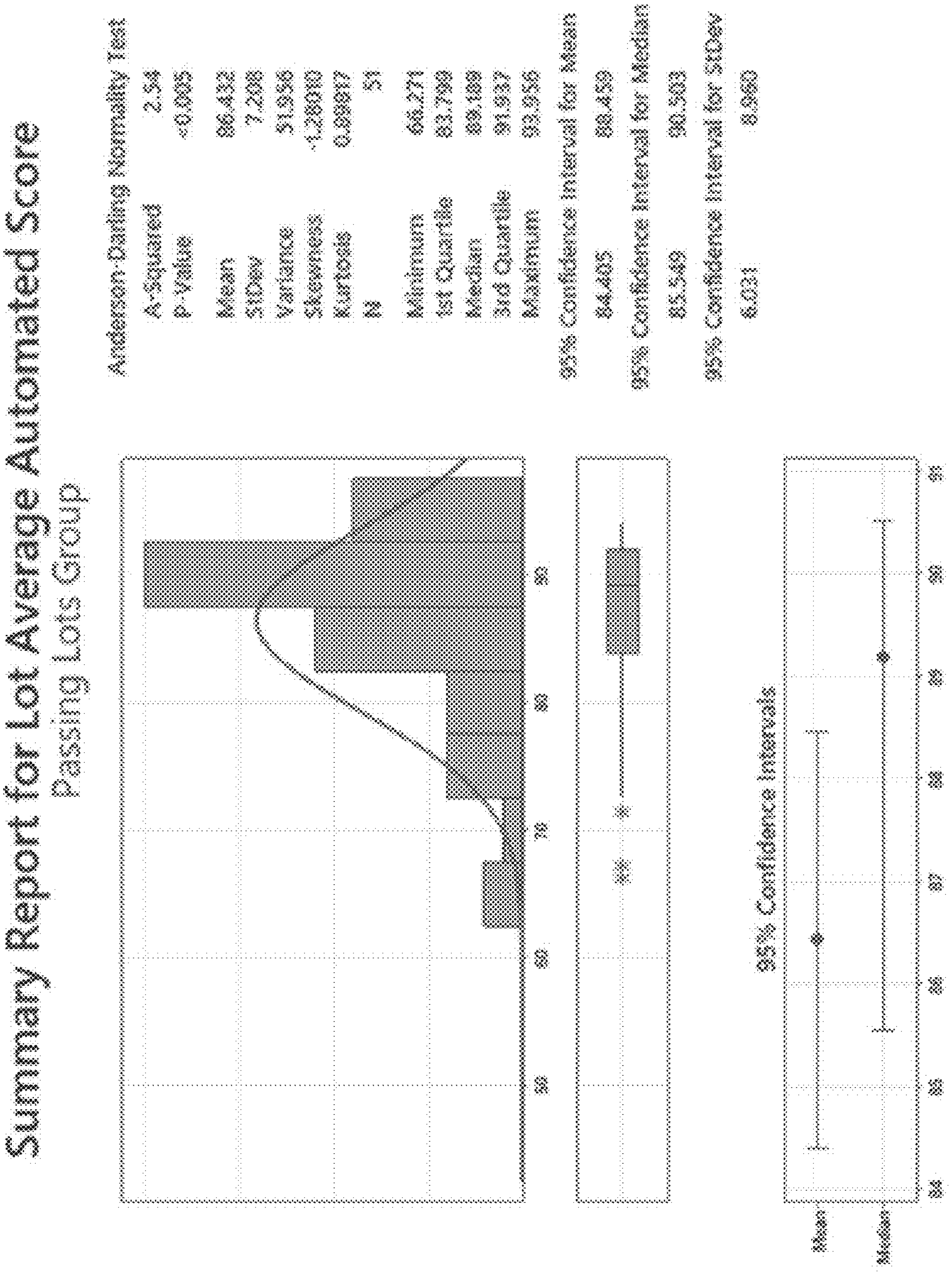
FIG. 16 is a histogram for passing nerve graft lots in the evaluation of one embodiment of the automated methods of the invention.

FIG. 16 is a histogram for passing nerve graft lots in the evaluation of one embodiment of the automated methods of the invention. The data are non-normal, have a left-skewed distribution, and have an upper boundary near the values obtained for the IHC Negative Control samples. This left-skewed distribution is likely due to the enzyme treatment step in the manufacturing process. It is expected that the manufacturing process will yield a high level of CSPG clearance. Due to the skew of the data (long left tail), the median and interquartile range were used to summarize the centering and spread of the data, and to identify outliers.

Figure 17:
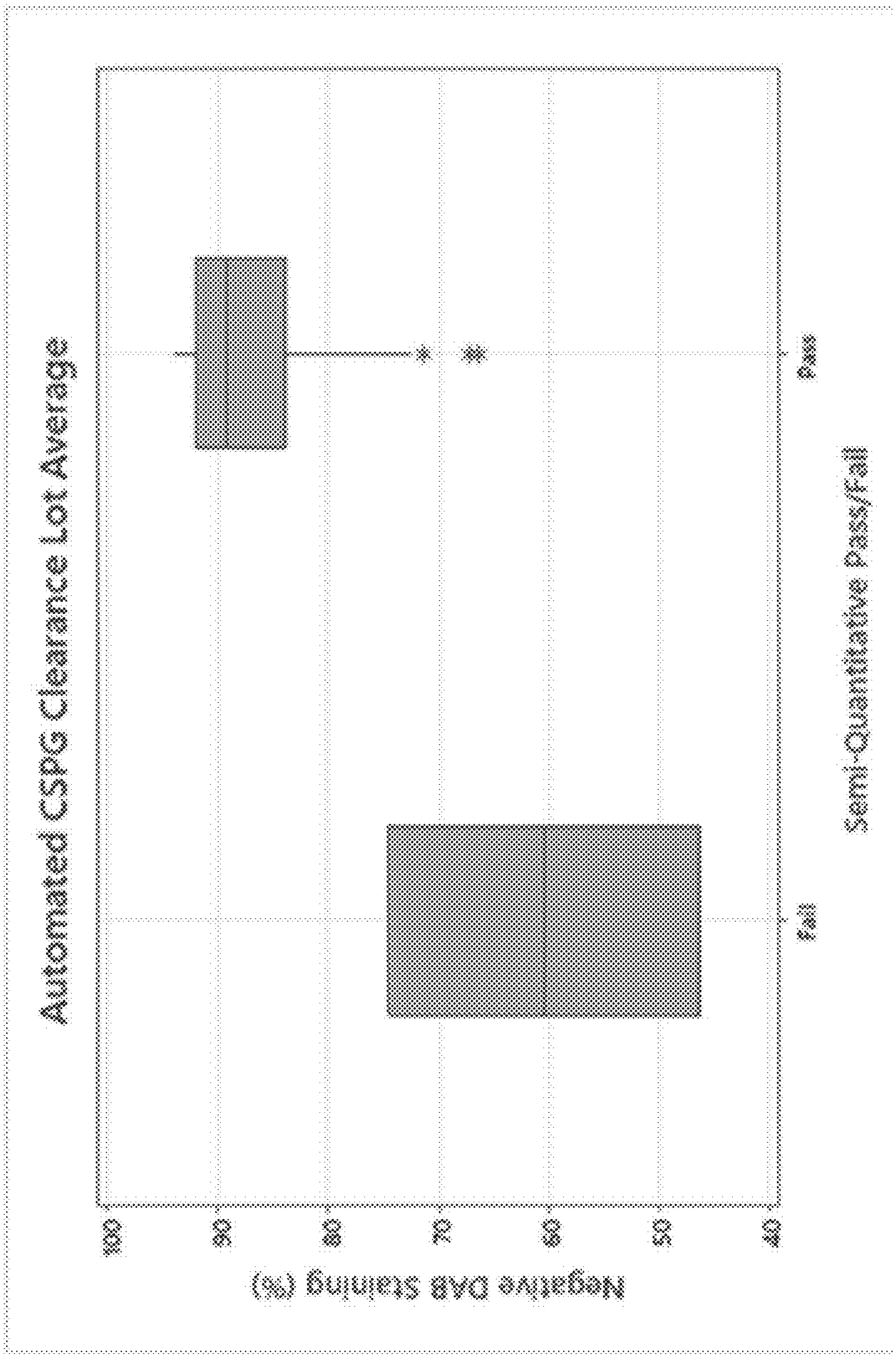
FIG. 17 shows a boxplot for passing processed nerve graft lots.

FIG. 17 shows a boxplot for passing processed nerve graft lots. Three outliers were identified in this group. Outliers are values that are at least 1.5 times the interquartile range (Q3-Q1) below the Q1 value. The interquartile range is 8.1, and the Q1 value is 83.8. This corresponds to a value of 71.7. Values below 71.7 are considered outliers. Three lots from the Passing Lot group and one lot from the Failing Lot group were identified as outliers. The four outlier lots and ten lots near the outlier range were reviewed to qualitatively evaluate the utility of 71.7% negative as the product acceptance criterion.

Evaluation of the two methods to determine potential acceptance criteria for the automated image analysis method—correlation to a semi-quantitative scoring scale and outlier analysis of data from passing lots—indicated that the outlier approach is validated. The value determined from the outlier analysis can be used to distinguish between lots with normal and abnormal levels of CSPG clearance. Lots that have an average score below 71.7% negative show abnormal levels of CSPG clearance. Lots that have an average score ≥71.7% and <80.0% negative show significant reduction of CSPG in the fascicles and/or non-specific staining in the endoneurium. This range can be used as an alert range to monitor the manufacturing process (e.g., trending of downward process shift), or to monitor the analytical method (e.g., trending of non-specific staining). Lots with an average score ≥80.0% show a normal level of CSPG clearance.

Accordingly, the analysis of the automated image analysis methods may be used to replace semiquantitative analysis methods for the evaluation of CSPG clearance in processed nerve graft tissue histological samples. The automated image analysis method provides a direct measure of DAB staining, which directly correlates to the presence of CSPG in the sample of nerve graft tissue. The method can also be used to evaluate the presence of CSPG in the donor-matched positive control sample of nerve graft tissue. Optimized stain separation was achieved by determining staining vectors from single-dye-stained sections of nerve graft tissue samples. The CSPG clearance metric, negative DAB staining (%), was established. This metric is more accurate and efficient as compared to semiquantitative methods. A product acceptance criterion was determined by performing outlier analysis on data from passing lots. A lot average score ≥71.7% negative DAB staining can be used as the product acceptance criteria. A lot average score ≥71.7% and <80.0% negative DAB staining can be used as an alert range.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

The invention claimed is:

1. An automated method for assessing chondroitin sulfate proteoglycan (CSPG) clearance from a processed nerve graft tissue, the method comprising:
- receiving a digital immunohistochemistry (IHC)-stained image of a nerve graft tissue, wherein, the IHC-stained image comprising at least hematoxylin staining and 3,3'-Diaminobenzidine (DAB) staining;
- generating a digital RGB color image of one or more selected regions of the stained image using an image conversion algorithm;
- performing, using an image analysis algorithm, an image processing step on the one or more selected regions to thereby separate image colors into a hematoxylin image channel, a DAB image channel, and a residual image channel;
- analyzing pixel intensity values of the image colors of one or more of the image channels based, at least in part, on image processing parameters to determine a number of pixels in one or more of a positive staining region, a negative staining region, and an unstained region in each image channel; and
- quantifying at least a proportion of the number of pixels analyzed as DAB positive-stained pixels in the positive staining region and DAB negative-stained pixels in the negative stained region in relation to a total number of pixels analyzed to thereby determine CSPG clearance in the processed nerve graft tissue.

2. The method of claim 1, wherein a calculated percent of DAB negative-stained pixels correlates to removal of CSPG in the processed nerve graft tissue.

3. The method of claim 1, wherein a calculated percent of DAB positive-stained pixels correlates to the presence of CSPG in the processed nerve graft tissue.

4. The method of claim 1, wherein the image processing step comprises a color deconvolution.

5. The method of claim 4, wherein, for the hematoxylin image channel, the image produced represents the hematoxylin staining in the IHC-stained image, and wherein the color deconvolution step separates the DAB staining from the IHC-stained image.

6. The method claim 4, wherein, for the DAB image channel, the image produced after the color deconvolution step represents the DAB staining in the IHC-stained image, and wherein the color deconvolution step separates the hematoxylin staining from the IHC-stained image.

7. The method of claim 4, wherein for the residual image channel, the image produced after the color deconvolution step represents the residual of the color deconvolution process.

8. The method of claim 1, wherein the analyzing step comprises analyzing the pixel intensity values in the image channel for any color in the range from 0 to 255 inclusive, wherein a pixel intensity value of 0 represents a darkest shade of color and a pixel intensity value of 255 represents a lightest shade of color.

9. The method claim 8, wherein the total pixels analyzed comprises the number of pixel intensity values between 0 and 235 inclusive analyzed.

10. The method of claim 8, wherein the positive staining regions comprise pixel intensity values between 0 and 180 inclusive.

11. The method of claim 10, wherein percent DAB positive-stained pixels is the proportion of pixels in the DAB image channel having an intensity value between 0 and 180 inclusive that represent positive DAB staining as compared to the total pixels analyzed.

12. The method of claim 8, wherein the negative staining regions comprise pixel intensity values between 181 and 235 inclusive.

13. The method of claim 12, wherein the percent negative DAB staining is the proportion of pixel intensity values in the DAB image channel with intensity value between 181 and 235 inclusive that represent negative DAB staining as compared to the total pixels analyzed.

14. The method of claim 8, wherein the unstained regions comprise pixels between 236 and 255 inclusive intensity values, wherein the pixels represent absence of extracellular matrix (ECM) tissue and are excluded from the analysis.

15. The method of claim 1, wherein the image processing parameters are determined via analysis of a library of images comprising single CSPG-stained sections of peripheral nerve graft tissue samples, wherein analysis of the library of single CSPG-stained sections of peripheral nerve graft tissue samples determines an optimal separation of image colors and a range of pixel intensity values.

16. The method of claim 15, wherein the image processing parameters comprise optimized staining vectors comprising a three-color vector matrix representing red, green, and blue absorbances in a saturated region of each individual image channel, wherein the optimized staining vectors optimize the method for application to processed nerve graft tissue.

17. The method of claim 1, wherein the processed peripheral nerve graft tissue comprises decellularized and sterile ECM processed from human peripheral nerve tissue having undergone an enzyme treatment step which cleaves sulfated sugar side chains from a CSPG protein core, wherein the immunohistochemistry staining is used to stain chondroitin sulfate side chains a brown color through a DAB immunoperoxidase reaction, and wherein evaluation of CSPG clearance is used for quality control testing for a processed nerve graft tissue production lot.

18. The method of claim 17, wherein the sulfated sugar side chains comprise one or more of chondroitin 4-sulfate, chondroitin 6-sulfate, and dermatan sulfate.

19. The method of claim 17, wherein a lot average percent negative DAB staining establishes an acceptance criteria for the production lot of processed nerve graft tissue.

20. The method of claim 1, further comprising batch processing of a plurality of digital IHC-stained images, wherein a batch of images are analyzed at once.

21. The method of claim 1, wherein the digital IHC-stained image is an extracted image in an uncompressed TIF file type of each individual nerve graft tissue sample extracted from a whole slide scan.

22. The method of claim 1, wherein the nerve graft tissue is peripheral nerve tissue.

23. The method of claim 1, wherein the nerve graft tissue is one of human, non-human mammal, fish, reptile, amphibian, or insect.

* * * * *